US011194998B2

(12) United States Patent
Koishida et al.

(10) Patent No.: US 11,194,998 B2
(45) Date of Patent: Dec. 7, 2021

(54) MULTI-USER INTELLIGENT ASSISTANCE

(71) Applicant: Microsoft Technology Licensing, LLC, Redmond, WA (US)

(72) Inventors: Kazuhito Koishida, Redmond, WA (US); Alexander A Popov, Kirkland, WA (US); Uros Batricevic, Redmond, WA (US); Steven Nabil Bathiche, Bellevue, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 15/657,822

(22) Filed: Jul. 24, 2017

(65) Prior Publication Data

US 2018/0233142 A1 Aug. 16, 2018

Related U.S. Application Data

(60) Provisional application No. 62/459,020, filed on Feb. 14, 2017, provisional application No. 62/482,165, filed on Apr. 5, 2017.

(51) Int. Cl.
*G10L 15/18* (2013.01)
*G06K 9/00* (2006.01)
(Continued)

(52) U.S. Cl.
CPC ........ *G06K 9/00261* (2013.01); *A61B 5/0205* (2013.01); *A61B 5/0507* (2013.01);
(Continued)

(58) Field of Classification Search
CPC ... G10L 15/22; G10L 2015/223; G10L 17/22; G10L 15/30; G10L 17/06; G10L 15/32;
(Continued)

(56) References Cited

U.S. PATENT DOCUMENTS 6,067,673 A 5/2000 Paese et al.
6,119,088 A 9/2000 Ciluffo
(Continued)

FOREIGN PATENT DOCUMENTS

CN 101216885 A 7/2008
CN 102547301 A 7/2012
(Continued)

OTHER PUBLICATIONS

"Train the Natural Language Processing Classifiers", Retrieved From <<https://www.mindmeld.com/docs/train_the_natural_language_processing_classifiers.html>>, Retrieved on: May 2, 2017, 10 Pages.
(Continued)

*Primary Examiner* — Richemond Dorvil
*Assistant Examiner* — Mark Villena
(74) *Attorney, Agent, or Firm* — Alleman Hall Creasman & Tuttle LLP

(57) ABSTRACT

An intelligent assistant records speech spoken by a first user and determines a self-selection score for the first user. The intelligent assistant sends the self-selection score to another intelligent assistant, and receives a remote-selection score for the first user from the other intelligent assistant. The intelligent assistant compares the self-selection score to the remote-selection score. If the self-selection score is greater than the remote-selection score, the intelligent assistant responds to the first user and blocks subsequent responses to all other users until a disengagement metric of the first user exceeds a blocking threshold. If the self-selection score is less than the remote-selection score, the intelligent assistant does not respond to the first user.

19 Claims, 11 Drawing Sheets

(51) Int. Cl.

| | |
|---|---|
| *G06K 9/72* | (2006.01) |
| *G06T 7/70* | (2017.01) |
| *G06K 9/62* | (2006.01) |
| *G06F 3/16* | (2006.01) |
| *G06N 20/00* | (2019.01) |
| *G06T 7/292* | (2017.01) |
| *H04W 4/33* | (2018.01) |
| *H04W 4/029* | (2018.01) |
| *A61B 5/11* | (2006.01) |
| *A61B 5/117* | (2016.01) |
| *A61B 5/00* | (2006.01) |
| *G01S 5/28* | (2006.01) |
| *G06F 1/3206* | (2019.01) |
| *G06F 1/3231* | (2019.01) |
| *G06F 1/324* | (2019.01) |
| *G06F 3/01* | (2006.01) |
| *G06F 3/03* | (2006.01) |
| *G06F 21/32* | (2013.01) |
| *G10L 17/04* | (2013.01) |
| *G10L 17/08* | (2013.01) |
| *H04L 12/58* | (2006.01) |
| *H04L 29/08* | (2006.01) |
| *H04N 5/232* | (2006.01) |
| *H04N 7/18* | (2006.01) |
| *H04N 21/422* | (2011.01) |
| *H04N 21/442* | (2011.01) |
| *G07C 9/28* | (2020.01) |
| *G06F 40/35* | (2020.01) |
| *G06F 40/211* | (2020.01) |
| *G06T 7/73* | (2017.01) |
| *G06T 7/246* | (2017.01) |
| *G01S 5/18* | (2006.01) |
| *G06T 7/60* | (2017.01) |
| *G10L 15/22* | (2006.01) |
| *G10L 15/28* | (2013.01) |
| *H04R 1/40* | (2006.01) |
| *H04R 3/00* | (2006.01) |
| *H04N 5/33* | (2006.01) |
| *G10L 15/02* | (2006.01) |
| *G06N 5/02* | (2006.01) |
| *G06N 5/04* | (2006.01) |
| *G10L 15/06* | (2013.01) |
| *G10L 15/24* | (2013.01) |
| *G10L 15/26* | (2006.01) |
| *G10L 15/19* | (2013.01) |
| *G10L 15/08* | (2006.01) |
| *G10L 15/32* | (2013.01) |
| *G10L 25/51* | (2013.01) |
| *H04L 29/06* | (2006.01) |
| *A61B 5/0205* | (2006.01) |
| *A61B 5/0507* | (2021.01) |
| *G01S 13/72* | (2006.01) |
| *G06F 21/35* | (2013.01) |
| *G08B 13/14* | (2006.01) |
| *G06F 3/0482* | (2013.01) |
| *G06F 3/0484* | (2013.01) |
| *H04N 21/231* | (2011.01) |
| *G06F 3/0488* | (2013.01) |
| *G06F 16/70* | (2019.01) |
| *A61B 5/05* | (2021.01) |
| *G01S 5/16* | (2006.01) |
| *G01S 11/14* | (2006.01) |
| *G01S 13/86* | (2006.01) |
| *G06N 3/04* | (2006.01) |
| *G08B 29/18* | (2006.01) |
| *G10L 17/00* | (2013.01) |
| *G07C 9/32* | (2020.01) |
| *H04N 5/247* | (2006.01) |
| *G01S 13/38* | (2006.01) |
| *G01S 13/88* | (2006.01) |

(52) U.S. Cl.
CPC ............. *A61B 5/117* (2013.01); *A61B 5/1113* (2013.01); *A61B 5/7475* (2013.01); *G01S 5/18* (2013.01); *G01S 5/28* (2013.01); *G01S 13/726* (2013.01); *G06F 1/324* (2013.01); *G06F 1/3206* (2013.01); *G06F 1/3231* (2013.01); *G06F 3/011* (2013.01); *G06F 3/017* (2013.01); *G06F 3/0304* (2013.01); *G06F 3/0482* (2013.01); *G06F 3/04842* (2013.01); *G06F 3/167* (2013.01); *G06F 21/32* (2013.01); *G06F 21/35* (2013.01); *G06F 40/211* (2020.01); *G06F 40/35* (2020.01); *G06K 9/00* (2013.01); *G06K 9/00214* (2013.01); *G06K 9/00255* (2013.01); *G06K 9/00288* (2013.01); *G06K 9/00295* (2013.01); *G06K 9/00342* (2013.01); *G06K 9/00362* (2013.01); *G06K 9/00711* (2013.01); *G06K 9/00771* (2013.01); *G06K 9/00973* (2013.01); *G06K 9/6254* (2013.01); *G06K 9/6255* (2013.01); *G06K 9/6289* (2013.01); *G06K 9/6296* (2013.01); *G06K 9/726* (2013.01); *G06N 5/025* (2013.01); *G06N 5/047* (2013.01); *G06N 20/00* (2019.01); *G06T 7/248* (2017.01); *G06T 7/292* (2017.01); *G06T 7/60* (2013.01); *G06T 7/70* (2017.01); *G06T 7/74* (2017.01); *G07C 9/28* (2020.01); *G08B 13/1427* (2013.01); *G10L 15/02* (2013.01); *G10L 15/063* (2013.01); *G10L 15/08* (2013.01); *G10L 15/18* (2013.01); *G10L 15/1815* (2013.01); *G10L 15/1822* (2013.01); *G10L 15/19* (2013.01); *G10L 15/22* (2013.01); *G10L 15/24* (2013.01); *G10L 15/26* (2013.01); *G10L 15/28* (2013.01); *G10L 15/32* (2013.01); *G10L 17/04* (2013.01); *G10L 17/08* (2013.01); *G10L 25/51* (2013.01); *H04L 51/02* (2013.01); *H04L 63/102* (2013.01); *H04L 67/12* (2013.01); *H04L 67/22* (2013.01); *H04N 5/23219* (2013.01); *H04N 5/332* (2013.01); *H04N 7/181* (2013.01); *H04N 7/188* (2013.01); *H04N 21/231* (2013.01); *H04N 21/42203* (2013.01); *H04N 21/44218* (2013.01); *H04N 21/44222* (2013.01); *H04R 1/406* (2013.01); *H04R 3/005* (2013.01); *H04W 4/029* (2018.02); *H04W 4/33* (2018.02); *A61B 5/05* (2013.01); *A61B 5/1118* (2013.01); *G01S 5/16* (2013.01); *G01S 11/14* (2013.01); *G01S 13/38* (2013.01); *G01S 13/867* (2013.01); *G01S 13/888* (2013.01); *G06F 3/0488* (2013.01); *G06F 16/70* (2019.01); *G06F 2203/0381* (2013.01); *G06F 2221/2111* (2013.01); *G06K 2209/09* (2013.01); *G06N 3/0445* (2013.01); *G06T 2207/10016* (2013.01); *G06T 2207/10024* (2013.01); *G06T 2207/20101* (2013.01); *G06T 2207/30196* (2013.01); *G06T 2207/30201* (2013.01); *G06T 2207/30204* (2013.01); *G06T 2207/30232* (2013.01); *G07C 9/32* (2020.01); *G08B 29/186* (2013.01); *G10L 17/00* (2013.01); *G10L 2015/0635* (2013.01); *G10L 2015/088* (2013.01); *G10L 2015/223*

(2013.01); *G10L 2015/225* (2013.01); *G10L 2015/228* (2013.01); *H04N 5/247* (2013.01); *Y02D 10/00* (2018.01)

(58) Field of Classification Search
CPC ....... G10L 15/08; G10L 17/005; G10L 15/20; G10L 15/26; G10L 17/00; G10L 21/0364; G10L 15/265; G06F 3/167; G06F 3/165; G06F 21/32

See application file for complete search history.

(56) References Cited

U.S. PATENT DOCUMENTS

| | | |
|---|---|---|
| 6,332,122 B1 | 12/2001 | Ortega et al. |
| 6,442,524 B1 | 8/2002 | Ecker et al. |
| 6,477,500 B2 | 11/2002 | Maes |
| 6,496,799 B1 | 12/2002 | Pickering |
| 6,574,601 B1 | 6/2003 | Brown et al. |
| 6,727,925 B1 | 4/2004 | Bourdelais |
| 6,728,679 B1 | 4/2004 | Strubbe et al. |
| 6,816,730 B2 | 11/2004 | Davies et al. |
| 6,873,953 B1 | 3/2005 | Lennig |
| 7,019,749 B2 | 3/2006 | Guo et al. |
| 7,050,110 B1 | 5/2006 | Lienhart et al. |
| 7,330,566 B2 | 2/2008 | Cutler |
| 7,475,010 B2 | 1/2009 | Chao |
| 7,610,365 B1 | 10/2009 | Kraft et al. |
| 7,716,056 B2 | 5/2010 | Weng et al. |
| 7,783,486 B2 | 8/2010 | Rosser et al. |
| 7,803,050 B2 | 9/2010 | Mao et al. |
| 8,139,945 B1 | 3/2012 | Amir et al. |
| 8,155,968 B2 | 4/2012 | Sugiyama et al. |
| 8,165,087 B2 | 4/2012 | Panabaker |
| 8,170,875 B2 | 5/2012 | Hetherington et al. |
| 8,213,689 B2 | 7/2012 | Yagnik et al. |
| 8,265,252 B2 | 9/2012 | Ducheneaut et al. |
| 8,326,627 B2 | 12/2012 | Kennewick et al. |
| 8,340,975 B1 | 12/2012 | Rosenberger |
| 8,374,879 B2 | 2/2013 | Falcon et al. |
| 8,453,402 B2 | 6/2013 | Huang |
| 8,457,959 B2 | 6/2013 | Kaiser |
| 8,543,402 B1 | 9/2013 | Ma |
| 8,639,762 B2 | 1/2014 | Rasmussen et al. |
| 8,644,842 B2 | 2/2014 | Arrasvuori et al. |
| 8,712,758 B2 | 4/2014 | Crouch et al. |
| 8,752,145 B1 | 6/2014 | Dotan et al. |
| 8,762,150 B2 | 6/2014 | Edgington et al. |
| 8,762,156 B2 | 6/2014 | Chen |
| 8,779,965 B2 | 7/2014 | Sentelle et al. |
| 8,805,691 B2 | 8/2014 | Genly |
| 8,861,924 B2 | 10/2014 | Meads et al. |
| 8,862,156 B2 | 10/2014 | Bell et al. |
| 8,885,882 B1 | 11/2014 | Reale et al. |
| 8,903,128 B2 | 12/2014 | Shet et al. |
| 8,913,103 B1 | 12/2014 | Sargin et al. |
| 8,942,986 B2 | 1/2015 | Cheyer et al. |
| 8,949,359 B2 | 2/2015 | Rasmussen et al. |
| 9,031,293 B2 | 5/2015 | Kalinli-Akbacak |
| 9,037,601 B2 | 5/2015 | Palay |
| 9,070,366 B1 | 6/2015 | Mathias et al. |
| 9,085,303 B2 | 7/2015 | Wolverton et al. |
| 9,119,512 B2 | 9/2015 | Martins, Jr. et al. |
| 9,123,330 B1 | 9/2015 | Sharifi et al. |
| 9,159,116 B2 | 10/2015 | Plagemann et al. |
| 9,171,542 B2 | 10/2015 | Gandrabur et al. |
| 9,230,544 B2 | 1/2016 | Kwon et al. |
| 9,245,497 B2 | 1/2016 | Pais et al. |
| 9,268,406 B2 | 2/2016 | Geisner et al. |
| 9,300,925 B1 | 3/2016 | Zhang |
| 9,307,355 B2 | 4/2016 | Nehrenz et al. |
| 9,311,932 B2 | 4/2016 | Carter |
| 9,318,105 B1 | 4/2016 | Khosla |
| 9,342,143 B1 | 5/2016 | Rhodes et al. |
| 9,348,990 B2 | 5/2016 | Chuaprasert et al. |
| 9,368,114 B2 | 6/2016 | Larson et al. |
| 9,372,851 B2 | 6/2016 | Hazen et al. |
| 9,378,740 B1 | 6/2016 | Rosen et al. |
| 9,380,177 B1 | 6/2016 | Rao et al. |
| 9,389,681 B2 | 7/2016 | Sankar et al. |
| 9,412,392 B2 | 8/2016 | Lindahl |
| 9,424,840 B1 | 8/2016 | Hart et al. |
| 9,466,286 B1* | 10/2016 | Hart .................. G10L 15/10 |
| 9,495,331 B2 | 11/2016 | Govrin et al. |
| 9,495,613 B2 | 11/2016 | Holz et al. |
| 9,507,977 B1 | 11/2016 | Mor et al. |
| 9,508,341 B1 | 11/2016 | Parlikar et al. |
| 9,514,227 B1 | 12/2016 | Garrett et al. |
| 9,558,749 B1 | 1/2017 | Secker-Walker et al. |
| 9,576,574 B2 | 2/2017 | van Os |
| 9,622,059 B2 | 4/2017 | Bouzid et al. |
| 9,626,352 B2 | 4/2017 | Allen et al. |
| 9,633,652 B2 | 4/2017 | Kumiawati et al. |
| 9,669,296 B1 | 6/2017 | Hibbert et al. |
| 9,747,896 B2 | 8/2017 | Kennewick et al. |
| 9,749,583 B1* | 8/2017 | Fineberg .............. H04N 7/147 |
| 9,761,055 B2 | 9/2017 | Miller |
| 9,767,616 B2 | 9/2017 | Miller |
| 9,842,299 B2 | 12/2017 | Stolarz et al. |
| 9,898,250 B1* | 2/2018 | Williams ............ G06F 3/167 |
| 9,965,247 B2* | 5/2018 | Jarvis ................. G06F 3/167 |
| 10,178,301 B1 | 1/2019 | Welbourne et al. |
| 10,276,149 B1 | 4/2019 | Liang et al. |
| 10,482,885 B1 | 11/2019 | Moniz |
| 10,599,390 B1 | 3/2020 | Brahmbhatt et al. |
| 2003/0103647 A1 | 6/2003 | Rui et al. |
| 2003/0131064 A1 | 7/2003 | Bell et al. |
| 2005/0182627 A1 | 8/2005 | Tanaka et al. |
| 2005/0216264 A1 | 9/2005 | Attwater et al. |
| 2005/0225427 A1 | 10/2005 | Bell et al. |
| 2005/0285774 A1 | 12/2005 | Wittenberg et al. |
| 2006/0028552 A1 | 2/2006 | Aggarwal et al. |
| 2006/0067536 A1 | 3/2006 | Culbert et al. |
| 2007/0024487 A1 | 2/2007 | Zemany et al. |
| 2007/0100480 A1 | 5/2007 | Sinclair et al. |
| 2007/0152157 A1 | 7/2007 | Page |
| 2007/0198245 A1 | 8/2007 | Kamatani et al. |
| 2007/0271086 A1 | 11/2007 | Peters et al. |
| 2008/0015864 A1 | 1/2008 | Ross et al. |
| 2008/0030345 A1 | 2/2008 | Austin et al. |
| 2008/0071547 A1 | 3/2008 | Prieto et al. |
| 2008/0077015 A1 | 3/2008 | Boric-Lubecke et al. |
| 2008/0195387 A1* | 8/2008 | Zigel ................... G10L 17/06 |
| | | 704/236 |
| 2008/0288251 A1 | 11/2008 | Cooper et al. |
| 2009/0066690 A1 | 3/2009 | Harrison |
| 2009/0303342 A1 | 12/2009 | Corcoran et al. |
| 2009/0319269 A1 | 12/2009 | Aronowitz |
| 2010/0073363 A1 | 3/2010 | Densham et al. |
| 2010/0100851 A1 | 4/2010 | Clark et al. |
| 2010/0179813 A1* | 7/2010 | Summerfield ........ G10L 17/14 |
| | | 704/246 |
| 2010/0195906 A1 | 8/2010 | Uliyar et al. |
| 2011/0010170 A1* | 1/2011 | Burns .................. G10L 15/22 |
| | | 704/231 |
| 2011/0119060 A1 | 5/2011 | Aronowitz |
| 2011/0184735 A1 | 7/2011 | Flaks et al. |
| 2011/0216090 A1 | 9/2011 | Woo et al. |
| 2011/0219339 A1 | 9/2011 | Densham |
| 2011/0298967 A1 | 12/2011 | Clavin et al. |
| 2011/0302535 A1 | 12/2011 | Clerc et al. |
| 2012/0026335 A1 | 2/2012 | Brown et al. |
| 2012/0253791 A1 | 10/2012 | Heck et al. |
| 2012/0265535 A1 | 10/2012 | Bryant-rich et al. |
| 2012/0268604 A1 | 10/2012 | Tree |
| 2013/0110519 A1 | 5/2013 | Cheyer et al. |
| 2013/0117377 A1 | 5/2013 | Miller |
| 2013/0212501 A1 | 8/2013 | Anderson et al. |
| 2013/0253936 A1 | 9/2013 | Harvey |
| 2013/0259456 A1 | 10/2013 | Viswanathan |
| 2013/0304479 A1 | 11/2013 | Teller et al. |
| 2013/0342568 A1 | 12/2013 | Ambrus et al. |
| 2014/0033071 A1 | 1/2014 | Gruber et al. |
| 2014/0067679 A1 | 3/2014 | O'Reilly et al. |
| 2014/0100997 A1 | 4/2014 | Mayerle et al. |
| 2014/0156276 A1 | 6/2014 | Nakano et al. |

(56) References Cited

U.S. PATENT DOCUMENTS

| | | |
|---|---|---|
| 2014/0160290 A1 | 6/2014 | Wu |
| 2014/0180629 A1 | 6/2014 | Dokmanic et al. |
| 2014/0214421 A1 | 7/2014 | Shriberg et al. |
| 2014/0214429 A1 | 7/2014 | Pantel |
| 2014/0222422 A1 | 8/2014 | Sarikaya et al. |
| 2014/0244263 A1 | 8/2014 | Pontual et al. |
| 2014/0272821 A1 | 9/2014 | Pitschel et al. |
| 2014/0330569 A1 | 11/2014 | Kolavennu et al. |
| 2014/0341440 A1 | 11/2014 | Walch |
| 2014/0365226 A1 | 12/2014 | Sinha |
| 2015/0016642 A1 | 1/2015 | Walsh et al. |
| 2015/0019714 A1 | 1/2015 | Shaashua et al. |
| 2015/0025887 A1 | 1/2015 | Sidi et al. |
| 2015/0032254 A1 | 1/2015 | Ishiguro |
| 2015/0032456 A1 | 1/2015 | Wait |
| 2015/0035976 A1 | 2/2015 | Mayuzumi |
| 2015/0102996 A1 | 4/2015 | Yim et al. |
| 2015/0134547 A1 | 5/2015 | Oikonomidis |
| 2015/0138332 A1 | 5/2015 | Cheng et al. |
| 2015/0149179 A1 | 5/2015 | Korbecki |
| 2015/0149182 A1 | 5/2015 | Kalns et al. |
| 2015/0162000 A1 | 6/2015 | Di censo et al. |
| 2015/0172285 A1 | 6/2015 | Lo et al. |
| 2015/0195666 A1 | 7/2015 | Massey et al. |
| 2015/0220244 A1 | 8/2015 | Vats et al. |
| 2015/0249664 A1 | 9/2015 | Talhami et al. |
| 2015/0278199 A1 | 10/2015 | Hazen et al. |
| 2015/0279368 A1* | 10/2015 | Contolini ............... G10L 15/08 704/246 |
| 2015/0340033 A1 | 11/2015 | Di fabbrizio et al. |
| 2015/0340040 A1 | 11/2015 | Mun et al. |
| 2015/0347114 A1 | 12/2015 | Yoon |
| 2015/0371639 A1 | 12/2015 | Foerster et al. |
| 2015/0382047 A1* | 12/2015 | Van Os ............... G06F 17/3084 725/38 |
| 2016/0019889 A1* | 1/2016 | Alvarez Guevara ... G10L 15/08 704/254 |
| 2016/0063989 A1* | 3/2016 | Deleeuw ............... G10L 15/22 345/473 |
| 2016/0086018 A1 | 3/2016 | Lemoff |
| 2016/0088043 A1 | 3/2016 | Jiang et al. |
| 2016/0092732 A1 | 3/2016 | Black |
| 2016/0110347 A1 | 4/2016 | Kennewick et al. |
| 2016/0138247 A1 | 5/2016 | Conway et al. |
| 2016/0148417 A1 | 5/2016 | Kim et al. |
| 2016/0155443 A1 | 6/2016 | Khan et al. |
| 2016/0171289 A1 | 6/2016 | Lee et al. |
| 2016/0173293 A1 | 6/2016 | Kennedy |
| 2016/0179831 A1 | 6/2016 | Gruber et al. |
| 2016/0187961 A1 | 6/2016 | Elibol et al. |
| 2016/0203002 A1 | 7/2016 | Kannan et al. |
| 2016/0210411 A1 | 7/2016 | Mentis |
| 2016/0217783 A1* | 7/2016 | Konuma ............... G10L 15/1822 |
| 2016/0225373 A1 | 8/2016 | Casado et al. |
| 2016/0234595 A1* | 8/2016 | Goran ............... H04R 3/002 |
| 2016/0234616 A1 | 8/2016 | Gateau |
| 2016/0253310 A1 | 9/2016 | Hazen et al. |
| 2016/0259623 A1 | 9/2016 | Sumner et al. |
| 2016/0283185 A1 | 9/2016 | Mclaren et al. |
| 2016/0313868 A1 | 10/2016 | Weng et al. |
| 2016/0342702 A1 | 11/2016 | Barve et al. |
| 2016/0358598 A1 | 12/2016 | Williams et al. |
| 2016/0360336 A1 | 12/2016 | Gross et al. |
| 2016/0380929 A1 | 12/2016 | Katis et al. |
| 2017/0013409 A1 | 1/2017 | Cerchio et al. |
| 2017/0025124 A1 | 1/2017 | Mixter et al. |
| 2017/0032021 A1 | 2/2017 | Watanachote |
| 2017/0032787 A1 | 2/2017 | Dayal |
| 2017/0039423 A1 | 2/2017 | Cork et al. |
| 2017/0039602 A1 | 2/2017 | Shi-nash et al. |
| 2017/0068423 A1 | 3/2017 | Napolitano et al. |
| 2017/0078573 A1 | 3/2017 | Chen et al. |
| 2017/0133011 A1* | 5/2017 | Chen ............... H04L 12/4625 |
| 2017/0140760 A1* | 5/2017 | Sachdev ............... G10L 17/04 |
| 2017/0169476 A1 | 6/2017 | Nomula et al. |
| 2017/0185375 A1 | 6/2017 | Martel et al. |
| 2017/0186290 A1 | 6/2017 | Li et al. |
| 2017/0194000 A1* | 7/2017 | Itani ............... G10L 15/22 |
| 2017/0206900 A1 | 7/2017 | Lee et al. |
| 2017/0213157 A1 | 7/2017 | Bugay et al. |
| 2017/0230705 A1 | 8/2017 | Pardue et al. |
| 2017/0236512 A1* | 8/2017 | Williams ............... G10L 15/22 381/79 |
| 2017/0242651 A1* | 8/2017 | Lang ............... H04R 29/007 |
| 2017/0249309 A1 | 8/2017 | Sarikaya |
| 2017/0255450 A1 | 9/2017 | Mullins et al. |
| 2017/0262472 A1* | 9/2017 | Goldenberg ............ G06F 21/32 |
| 2017/0269975 A1* | 9/2017 | Wood ............... G10L 15/22 |
| 2017/0278480 A1 | 9/2017 | Sung et al. |
| 2017/0286530 A1 | 10/2017 | Paruchuri et al. |
| 2017/0287490 A1* | 10/2017 | Biswal ............... G10L 15/20 |
| 2017/0315208 A1 | 11/2017 | Sadr |
| 2017/0322939 A1 | 11/2017 | Byron et al. |
| 2017/0357637 A1 | 12/2017 | Nell et al. |
| 2017/0359666 A1 | 12/2017 | Lyren et al. |
| 2018/0009118 A1 | 1/2018 | Yamaga et al. |
| 2018/0047394 A1* | 2/2018 | Tian ............... G10L 15/24 |
| 2018/0048768 A1* | 2/2018 | Spittle ............... H04M 9/082 |
| 2018/0074785 A1 | 3/2018 | Ohmura |
| 2018/0090143 A1 | 3/2018 | Saddler et al. |
| 2018/0091782 A1 | 3/2018 | Bashkin |
| 2018/0096696 A1* | 4/2018 | Mixter ............... G10L 15/08 |
| 2018/0107930 A1 | 4/2018 | Aggarwal et al. |
| 2018/0158454 A1* | 6/2018 | Campbell ............... G10L 15/22 |
| 2018/0199123 A1 | 7/2018 | Rao et al. |
| 2018/0218080 A1 | 8/2018 | Krishnamurthy et al. |
| 2018/0231653 A1 | 8/2018 | Pradeep et al. |
| 2018/0232201 A1 | 8/2018 | Holtmann |
| 2018/0232563 A1 | 8/2018 | Albadawi et al. |
| 2018/0232571 A1 | 8/2018 | Bathiche et al. |
| 2018/0232608 A1 | 8/2018 | Pradeep et al. |
| 2018/0232645 A1 | 8/2018 | Finkelstein et al. |
| 2018/0232662 A1 | 8/2018 | Solomon et al. |
| 2018/0232902 A1 | 8/2018 | Albadawi et al. |
| 2018/0233132 A1 | 8/2018 | Herold et al. |
| 2018/0233139 A1 | 8/2018 | Finkelstein et al. |
| 2018/0233140 A1 | 8/2018 | Koishida et al. |
| 2018/0233141 A1 | 8/2018 | Solomon et al. |
| 2018/0233145 A1 | 8/2018 | Bathiche et al. |
| 2018/0260680 A1 | 9/2018 | Finkelstein et al. |
| 2018/0293221 A1 | 10/2018 | Finkelstein et al. |
| 2018/0314689 A1 | 11/2018 | Wang et al. |
| 2018/0333862 A1 | 11/2018 | Hayashi |
| 2019/0057703 A1 | 2/2019 | Zeinstra |
| 2020/0012906 A1 | 1/2020 | Albadawi et al. |
| 2020/0042839 A1 | 2/2020 | Herold et al. |
| 2020/0104653 A1 | 4/2020 | Solomon et al. |

FOREIGN PATENT DOCUMENTS

| | | |
|---|---|---|
| CN | 102760434 A | 10/2012 |
| CN | 103209030 A | 7/2013 |
| CN | 103262156 A | 8/2013 |
| CN | 103285591 A | 9/2013 |
| CN | 104272709 A | 1/2015 |
| CN | 104321730 A | 1/2015 |
| CN | 104423537 A | 3/2015 |
| CN | 104782121 A | 7/2015 |
| CN | 104838336 A | 8/2015 |
| CN | 105070288 A | 11/2015 |
| CN | 105278681 A | 1/2016 |
| CN | 105389307 A | 3/2016 |
| CN | 105408891 A | 3/2016 |
| CN | 105556917 A | 5/2016 |
| CN | 105611500 A | 5/2016 |
| CN | 106104517 A | 11/2016 |
| CN | 106157952 A | 11/2016 |
| CN | 106164921 A | 11/2016 |
| CN | 106340299 A | 1/2017 |
| EP | 2947476 A1 | 11/2015 |
| GB | 2522922 A | 8/2015 |
| KR | 1020070016280 A | 2/2007 |
| KR | 20150101088 A | 9/2015 |
| WO | 2007018523 A2 | 2/2007 |

(56) References Cited

FOREIGN PATENT DOCUMENTS

| WO | 2010104772 A1 | 9/2010 |
|---|---|---|
| WO | 2013061268 A2 | 5/2013 |
| WO | 2015012449 A1 | 1/2015 |
| WO | 2016043005 A1 | 3/2016 |
| WO | 2016114922 A1 | 7/2016 |
| WO | 2016157662 A1 | 10/2016 |
| WO | 2016162678 A1 | 10/2016 |
| WO | 2016205419 A1 | 12/2016 |

OTHER PUBLICATIONS

Ballan, et al. "Event Detection and Recognition for Semantic Annotation of Video", In Journal of Multimedia Tools and Applications, vol. 51, Issue 1, Nov. 10, 2010, pp. 279-302.
"Application Filed in U.S. Appl. No. 15/173,349", filed Jun. 3, 2016, 34 Pages.
"Application Filed in U.S. Appl. No. 15/395,961", filed Dec. 30, 2016, 79 Pages.
Beltagy, et al., "Improved Semantic Parsers for If-Then Statements", In Proceedings of the 54th Annual Meeting of the Association for Computational Linguistics, vol. 1, Aug. 7, 2016, pp. 726-736.
Boakye, et al., "Overlapped Speech Detection for Improved Speaker Diarization in Multiparty Meetings", In Proceedings of IEEE International Conference on Acoustics, Speech and Signal Processing, Mar. 31, 2008, 4 Pages.
Zotkin, et al., "Joint Audio-Visual Tracking Using Particle Filters", In EURASIP Journal on Applied Signal Processing, vol. 2002, Issue 1, Jan. 2002, pp. 1154-1164.
Fossard, et al., "Between Anaphora and Deixis . . . The Resolution of the Demonstrative Noun Phrase that N", In Journal of Language and Cognitive Processes, vol. 27, Issue 9, Nov. 2, 2011, 3 Pages.
Cho, et al., "A Multi-Sensor Fusion System for Moving Object Detection and Tracking in Urban Driving Environments", In IEEE International Conference on Robotics & Automation, May 31, 2014, 8 Pages.
Goncalves, et al., "Assessing Users' Emotion at Interaction Time: A Multimodal Approach With Multiple Sensors", In Proceedings of Soft Computing, vol. 21, Issue 18, Mar. 21, 2016, 8 Pages.
Goswami, et al., "A Reviewon Low Light Image Enhancement Using Image Processing Technique", In International Journal of Technical Research, vol. 5, Issue 1, Mar. 2016, pp. 60-62.
He, et al., "Sensor scheduling for target tracking: A Monte Carlo sampling approach", In Journal of Digital Signal Processing, vol. 16, Issue 5, Sep. 2006, pp. 533-545.
Huijbregts, et al., "Speech Overlap Detection in a Two-Pass Speaker Diarization System", In Proceedings of 10th Annual Conference of the International Speech Communication, Sep. 6, 2009, pp. 1063-1066.
Kabadjov, Mijail Alexandrov., "A Comprehensive Evaluation of Anaphora Resolution and Discourse-new Classification", In thesis of University of Essex, May 2007, 266 Pages.
Wheeler, et al., "Face Recognition at a Distance", In Publication of Springer, Jan. 2011, pp. 353-381.
Toutanova, et al., "Compositional Learning of Embeddings for Relation Paths in Knowledge Bases and Text", In Proceedings of the 54th Annual Meeting of the Association for Computational Linguistics, Aug. 7, 2016, pp. 1434-1444.
Mk, et al., "Ambiguities in Natural Language Processing", In International Journal of Innovative Research in Computer and Communication Engineering, vol. 2, Special Issue 5, Oct. 2014, pp. 392-394.
Sinha, et al., "An Analysis Engine for Dependable Elicitation on Natural Language Use Case Description and its Application to Industrial Use Cases", In IBM Research Report, RC242712, Dec. 18, 2008, 12 Pages.
Quirk, et al., "Language to Code: Learning Semantic Parsers for If-This-Then-That Recipes", In Proceedings of the 53rd Annual Meeting of the Association for Computational Linguistics, Jul. 26, 2015, pp. 878-888.
Rizwan, et al., "Local Enhancement for Robust Face Detection in Poor SNR Images", In International Journal of Computer Science and Network Security, vol. 9, Issue 6, Jun. 2009, pp. 93-96.
Kang, et al., "Detection and Tracking of Moving Objects from Overlapping EO and IR Sensors", In Conference on Computer Vision and Pattern Recognition Workshop, Jun. 27, 2004, 6 Pages.
Liu, et al., "Reliable Multiple Object Tracking under Heavy Occlusions", In Intelligence Information Processing and Trusted Computing (IPTC), 2010 International Symposium, Oct. 28, 2010, 3 Pages.
Pan, et al., "Robust Occlusion Handling in Object Tracking", In IEEE Conference on Computer Vision and Pattern Recognition, Jun. 17, 2007, 8 Pages.
Wagner, Martin, "Tracking with Multiple Sensors" By Faculty of Computer Science at the Technical University of Munich, Sep. 12, 2004, 202 Pages.
Gebhart, Andrew, "How to bring Alexa into every room of your home", https://www.cnet.com/how-to/how-to-install-alexa-in-every-room-of-your-home/, Published on: Feb. 2, 2017, 8 pages.
"Using Multiple Alexa Devices", https://www.amazon.com/gp/help/customer/display.html?nodeId=202013740, Published on: Apr. 24, 2017, 2 pages.
"Amazon Alexa's 'Follow-Up Mode' enables successive requests without trigger word", Retrieved from: https://appleinsider.com/articles/18/03/09/amazon-alexas-follow-up-mode-enables-successive-requests-without-trigger-word, Mar. 9, 2018, 7 Pages.
"Multiple Agents (each trained for different domain) for One Chat Bot?", Retrieved from: https://discuss.api.ai/t/multiple-agents-each-trained-for-different-domain-for-one-chat-bot/1002, Jul. 1, 2016, 1 Page.
"SARA: The Socially Aware Robot Assistant", Retrieved from: https://web.archive.org/web/20160707141922/http://articulab.hcii.cs.cmu.edu:80/projects/sara/, Jul. 7, 2017, 10 Pages.
Arsikere, et al., "Computationally-efficient Endpointing Features for Natural Spoken Interaction with Personal-assistant Systems", In Proceedings of IEEE International Conference on Acoustics, Speech and Signal Processing, May 4, 2014, pp. 3241-3245.
Ferrer, et al., "Is the Speaker Done Yet? Faster and More Accurate End-of-Utterance Detection using Prosody", In the proceedings of Seventh International Conference on Spoken Language Processing, Sep. 16, 2002, pp. 2061-2064.
Kalal, et al., "Face-TLD: Tracking-Learning-Detection Applied to Caces", In Proceedings of 17th IEEE International Conference on Image Processing, Sep. 26, 2010, pp. 3789-3792.
Kozhaya, Joe, "10 Steps to Train an Effective Chatbot and its Machine Learning Models", Retrieved from: https://developer.ibm.com/dwblog/2016/10-steps-train-chat-bot-chatbot-machine-learning/, Dec. 12, 2016, 7 Pages.
Lacharite, Noelle, "Updated: Alexa Skills Kit Fact Template: Step-by-Step Guide to Build a Fact Skill", Retrieved from: https://developer.amazon.com/blogs/post/Tx3DVGG0K0TPUGQ/New-Alexa-Skills-Kit-Template:-Step-by-Step-Guide-to-Build-a-Fact-Skill, Mar. 29, 2016, 33 Pages.
Li, Bo, "A Multiple-Camera System Calibration Toolbox Using a Feature Descriptor-based Calibration Pattern", In Proceedings of IEEE International Conference on Intelligent Robots and Systems, Nov. 3, 2013, pp. 1301-1307.
Mengusoglu, Erhan, "Confidence Measures for Speech/Speaker Recognition and Applications on Turkish LVCSR", Retrieved from https://web.archive.org/web/20040619044603/http://www.tcts.fpms.ac.be/publications/phds/mengusoglu/thesis_mengus.pdf, Apr. 20, 2004, 143 Pages.
Mikolajczyk, K, et al., "Face Detection and Tracking in a Video by Propagating Detection Probabilities", In Proceedings of IEEE Transactions on Pattern Analysis and Machine Intelligence, vol. 25, Issue 10, Oct. 1, 2003, pp. 1215-1228.
Panzarino, Matthew, "Here's an Actual 3D Indoor Map of a Room Captured With Google's Project Tango Phone", Retrieved From: https://techcrunch.com/2014/02/21/heres-an-actual-3d-indoor-map-of-a-room-captured-with-googles-project-tango-phone/, Feb. 21, 2014, 6 Pages.

(56) References Cited

OTHER PUBLICATIONS

"International Search Report and Written Opinion Issued in PCT Application No. PCT/US2018/017139", dated May 8, 2018, 13 Pages.
"International Search Report and Written Opinion Issued in PCT Application No. PCT/US2018/017140", dated May 18, 2018, 12 Pages.
"International Search Report and Written Opinion Issued in PCT Application No. PCT/US2018/017506", dated May 4, 2018, 13 Pages.
"International Search Report and Written Opinion Issued in PCT Application No. PCT/US2018/017508", dated May 8, 2018, 13 Pages.
"International Search Report and Written Opinion Issued in PCT Application No. PCT/US2018/017509", dated May 11, 2018, 11 Pages.
"International Search Report and Written Opinion Issued in PCT Application No. PCT/US2018/017510", dated Apr. 20, 2018, 14 Pages.
"International Search Report and Written Opinion Issued in PCT Application No. PCT/US2018/017511", dated May 17, 2018, 12 Pages.
"International Search Report and Written Opinion Issued in PCT Application No. PCT/US2018/017512", dated May 4, 2018, 15 Pages.
"International Search Report and Written Opinion Issued in PCT Application No. PCT/US2018/017513", dated Apr. 12, 2018, 15 Pages.
"International Search Report and Written Opinion Issued in PCT Application No. PCT/US2018/017514", dated May 17, 2018, 12 Pages.
"International Search Report and Written Opinion Issued in PCT Application No. PCT/US2018/017515", dated May 9, 2018, 12 Pages.
"International Search Report and Written Opinion Issued in PCT Application No. PCT/US2018/017517", dated May 11, 2018, 12 Pages.
Porcheron, et al., "Do Animals Have Accents?: Talking with Agents in Multi-Party Conversation", In Proceedings of 20th ACM Conference on Computer-Supported cooperative Work and Social Computing, Feb. 25, 2017, 14 Pages.
Pullen, John Patrick., "Amazon Echo Tip: How to Add Multiple Users ! Time", Retrieved from http://time.com/4668359/amazon-echo-alexa-multiple-accounts/, Feb. 13, 2017., 3 Pages.
Xiang, Li, "Improving Knowledge Base Population With Information Extraction", A Thesis Submitted in Partial fulfillment of the Requirements of the University of New York for the Degree of Doctor of Philosophy, May 2016, 131 Pages.
Yamamoto, S, et al., "Algorithm Optimizations for Low-Complexity Eye Tracking", In Proceedings of IEEE International Conference on Systems, Man, and Cybernetics, Oct. 2009, pp. 18-22.
Yun-Nung, Chen, "Unsupervised Learning and Modeling of Knowledge and Intent for Spoken Dialogue Systems", In Proceedings of the 53rd Annual Meeting of the Association for Computational Linguistics, Jul. 28, 2015, 8 Pages.
Zhang, et al., "A Joint Model of Intent Determination and Slot Filling for Spoken Language Understanding", In Proceedings of the Twenty-Fifth International Joint Conference on Artificial Intelligence, Jul. 9, 2016, pp. 2993-2999.
"Non Final Office Action Issued in U.S. Appl. No. 15/636,422", dated Sep. 4, 2018, 11 Pages.
"Non Final Office Action Issued in U.S. Appl. No. 15/640,251", dated Oct. 15, 2018, 22 Pages.
"Non Final Office Action Issued in U.S. Appl. No. 15/646,871", dated Dec. 19, 2018, 22 Pages.
"Non Final Office Action Issued in U.S. Appl. No. 15/656,994", dated Jan. 22, 2019, 8 Pages.
"Non Final Office Action Issued in U.S. Appl. No. 15/657,031", dated Oct. 5, 2018, 16 Pages.
"Non Final Office Action Issued in U.S. Appl. No. 15/832,656", dated Feb. 7, 2019, 8 Pages.
"Non Final Office Action Issued in U.S. Appl. No. 15/682,407", dated Jun. 26, 2019, 15 Pages.
"Final Office Action Issued in U.S. Appl. No. 15/640,251", dated Apr. 2, 2019, 22 Pages.
Miro, et al., "Speaker Diarization: A review of Recent Research", In the Proceedings of IEEE Transactions on Audio, Speech and Language Processing, vol. 20, Issue 2, Feb. 1, 2012, 15 Pages.
Moattar, et al., "A Review on Speaker Diarization Systems and Approaches", In the Publication of Speech Communication, vol. 54, Issue 10, Dec. 12, 2010, 39 Pages.
"International Search Report & Written Opinion for PCT Patent Application No. PCT/US2018/062384", dated Feb. 15, 2019, 12 Pages.
Yu, et al., "Smart Meeting Systems: A Survey of State of the Art and Open Issues", In the Proceedings of ACM Computing Surveys, vol. 42, No. 2, Mar. 5, 2010, 20 Pages.
"Final Office Action Issued in U.S. Appl. No. 15/646,871", dated Apr. 19, 2019, 22 Pages.
"Non Final Office Action Issued in U.S. Appl. No. 15/682,425", dated May 6, 2019, 12 Pages.
"U.S. Appl. No. 15/885,518", filed Jan. 31, 2018, 40 Pages.
"Non Final Office Action Issued in U.S. Appl. No. 15/640,251", dated Sep. 12, 2019, 21 Pages.
"Non-Final Office Action Issued in U.S. Appl. No. 15/646,871", dated Sep. 3, 2019, 23 Pages.
"Final Office Action Issued in U.S. Appl. No. 15/832,656", dated Aug. 23, 2019, 10 Pages.
"International Search Report and Written Opinion Issued in PCT Application No. PCT/US2019/022836", dated Jun. 24, 2019, 15 Pages.
Constine, Jose, "Instagram launches selfie filters, copying the last big Snapchat feature", Retrieved from https://techcrunch.com/2017/05/16/instagram-face-filters/, May 16, 2017, 8 Pages.
"International Search Report and Written Opinion Issued in PCT Application No. PCT/US2019/029558", dated Jun. 28, 2019, 10 Pages.
"Office Action Issued in European Patent Application No. 18707800.1", dated Jun. 4, 2020, 4 Pages.
"Office Action Issued in European Patent Application No. 18708508.9", dated May 28, 2020, 6 Pages.
"Non Final Office Action Issued in U.S. Appl. No. 15/640,113", dated May 14, 2020, 13 Pages.
"Non Final Office Action Issued in U.S. Appl. No. 15/640,201", dated May 27, 2020, 11 Pages.
"Notice of Allowance Issued in U.S. Appl. No. 15/832,656", dated Apr. 22, 2020, 8 Pages.
"Notice of Allowance Issued in U.S. Appl. No. 15/832,672", dated Jun. 2, 2020, 11 Pages.
"Non Final Office Action Issued in U.S. Appl. No. 15/936,076", dated Apr. 15, 2020, 23 Pages.
"Notice of Allowance Issued in U.S. Appl. No. 16/573,677", dated Nov. 6, 2019, 9 Pages.
"Non Final Office Action Issued in U.S. Appl. No. 15/832,656", dated Jan. 6, 2020, 9 Pages.
"Non Final Office Action Issued in U.S. Appl. No. 16/005,470", dated Feb. 24, 2020, 11 Pages.
"Final Office Action Issued in U.S. Appl. No. 15/646,871", dated Jan. 21, 2020, 23 Pages.
"Final Office Action Issued in U.S. Appl. No. 15/640,251", dated Jan. 30, 2020, 21 Pages.
"Non Final Office Action Issued in U.S. Appl. No. 15/646,871", dated Jul. 1, 2020, 24 Pages.
"Notice of Allowance Issued in U.S. Appl. No. 15/640,251", dated Jul. 31, 2020, 11 Pages.
"Final Office Action Issued in U.S. Appl. No. 16/005,470", dated Sep. 4, 2020, 15 Pages.
Sarikaya, Ruh, "The Technology Behind Personal Digital Assistants: An Overview of the System Architecture and key Components", In Journal of IEEE Signal Processing Magazine, vol. 34, Issue 1, Jan. 11, 2017, pp. 67-81.

(56) References Cited

OTHER PUBLICATIONS

"Non Final Office Action Issued In U.S. Appl. No. 15/980,631", dated Sep. 18, 2020, 12 Pages.
"Office Action Issued in European Patent Application No. 18706104.9", dated Sep. 21, 2020, 4 Pages.
"Non Final Office Action Issued In U.S. Appl. No. 16/700,308", dated Sep. 25, 2020, 18 Pages.
"First Office Action and Search Report Issued in Chinese Patent Application No. 201880011885.1", dated Feb. 1, 2021, 16 Pages.
"Non Final Office Action Issued in U.S. Appl. No. 16/599,426", dated Jan. 12, 2021, 10 Pages.
"First Office Action and Search Report Issued in Chinese Patent Application No. 201880011970.8", dated Feb. 2, 2021, 15 Pages.
"First Office Action and Search Report Issued in Chinese Patent Application No. 201880011578.3", dated Feb. 2, 2021, 12 Pages.
"First Office Action and Search Report Issued in Chinese Patent Application No. 201880011967.6", dated Feb. 2, 2021, 13 Pages.
"First Office Action and Search Report Issued in Chinese Patent Application No. 201880012028.3", dated Feb. 2, 2021, 13 Pages.
"Second Office Action Issued in Chinese Patent Application No. 201880011578.3", dated Jun. 28, 2021, 6 Pages.
"Second Office Action Issued in Chinese Patent Application No. 201880011967.6", dated Jun. 25, 2021, 6 Pages.
"Second Office Action Issued in Chinese Patent Application No. 201880012028.3", dated: Jun. 25, 2021, 8 Pages.
"Non Final Office Action Issued in U.S. Appl. No. 16/005,470", dated Sep. 3, 2021, 9 Pages.
"Office Action Issued in European Patent Application No. 18706370.6", dated Aug. 16, 2021, 5 Pages.
"First Office Action and Search Report Issued in Chinese Patent Application No. 201880011716.8", dated Sep. 15, 2021, 11 Pages.
"Notice of Allowance Issued in Chinese Patent Application No. 201880011910.6", dated Sep. 3, 2021, 11 Pages.
Lin, et al., "A Face Tracking Method Using Feature Point Tracking", In Proceedings of the International Conference on Information Security and Intelligent Control, Aug. 14, 2012, pp. 210-213.
Ma, et al., "A Fast and Robust Face Detection and Tracking Algorithm", In Proceedings of the IEEE International Conference on Signal Processing, Communications and Computing, Aug. 5, 2014, pp. 446-449.
Wang, Changjun, "Research on Video Based Object Detection and Tracking", In Chinese Master's Theses Full-text Database Information Technology Edition, Apr. 2006, 119 pages.
"Office Action Issued in Indian Patent Application No. 201947029577", dated Oct. 8, 2021, 6 Pages.

* cited by examiner

MULTI-USER INTELLIGENT ASSISTANCE

CROSS REFERENCE TO RELATED APPLICATIONS

This application claims priority to U.S. Provisional Patent Application No. 62/459,020 filed Feb. 14, 2017, and to U.S. Provisional Patent Application No. 62/482,165 filed Apr. 5, 2017, the entirety of which are hereby incorporated herein by reference.

BACKGROUND

Interacting with computing systems via natural interactions, such as one or more of voice recognition, text, gesture recognition, motion detection, gaze detection, intent recognition, brain activity assessment, text, the state of a home automated device, etc., enables natural user interface experiences. As the volume of digital information and the numbers of computing devices increase, managing such natural user interaction interfaces to provide positive user experiences can prove challenging.

SUMMARY

An intelligent assistant records speech spoken by a first user and determines a self-selection score for the first user. The intelligent assistant sends the self-selection score to another intelligent assistant, and receives a remote-selection score for the first user from the other intelligent assistant. The intelligent assistant compares the self-selection score to the remote-selection score. If the self-selection score is greater than the remote-selection score, the intelligent assistant responds to the first user and blocks subsequent responses to all other users until a disengagement metric of the first user exceeds a blocking threshold. If the self-selection score is less than the remote-selection score, the intelligent assistant does not respond to the first user.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

The present disclosure relates generally to systems, methods, and logical constructs for providing intelligent assistance to users. In some examples, a variety of sensor data may be utilized to intelligently determine the content and/or timing of messages communicated to users and/or the performance of actions. In some examples natural language inputs, such as user commands and other utterances, may be received and processed. For some scenarios in which multiple devices are configured to provide intelligent assistance in a use environment occupied by multiple entities, each device may selectively respond or block responses to different users based on a variety of use conditions. Further, data from one or more sensors may be processed to generate identity, location/position, status/activity, and/or other information related to one or more entities within range of a sensor. Statistical probabilities based on current and past data may be utilized to generate confidence values associated with entity information.

Figure 1:
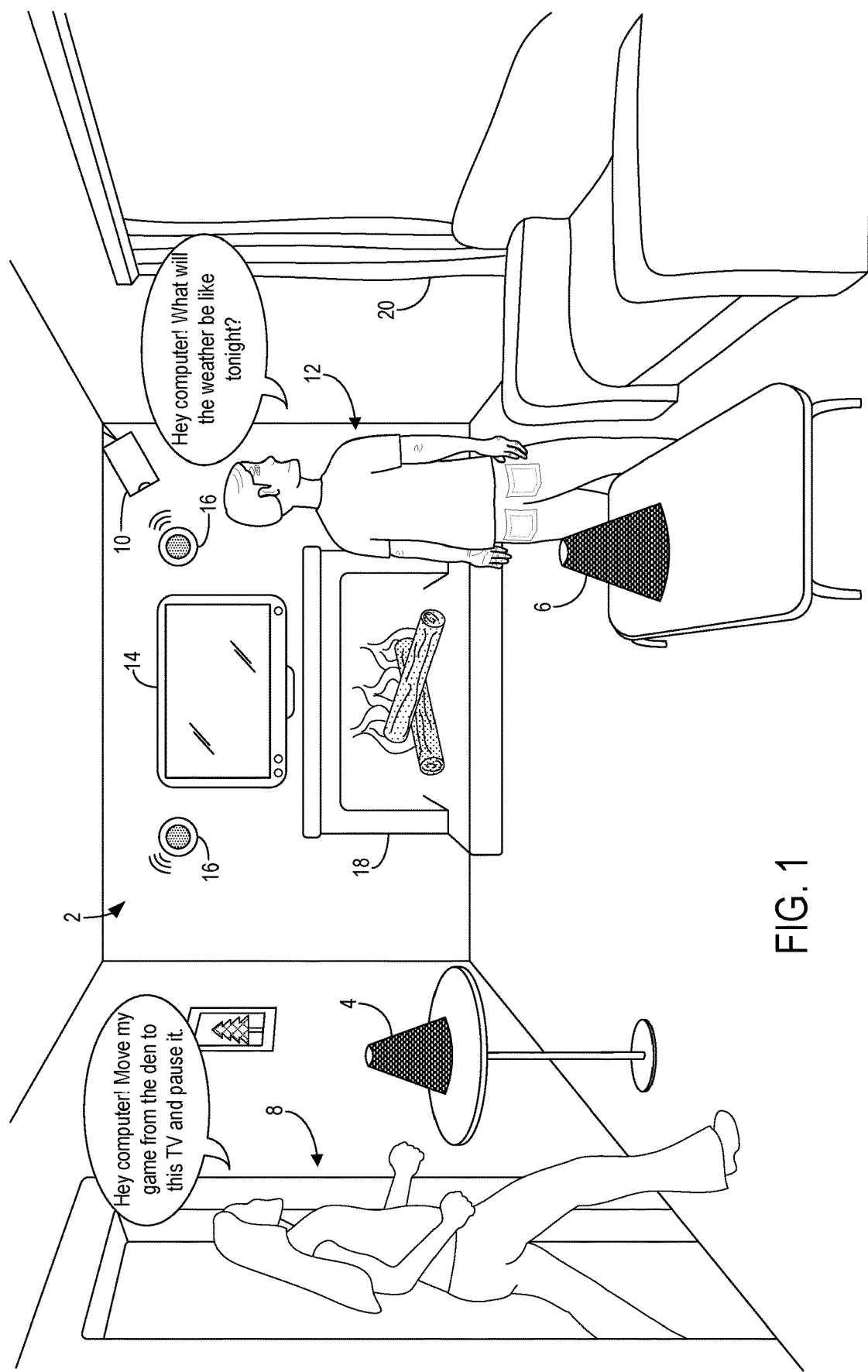
FIG. 1 shows an example environment with an intelligent assistant computer in the form of an all-in-one computing device according to an example of the present disclosure.

FIG. 1 illustrates a use environment in the form of a living room 2, in which multiple intelligent assistant computers are located. The intelligent assistant computers assume the form of an all-in-one computing device 4 and an all-in-one computing device 6, both of which may be configured to perform myriad functions. In some examples, computing devices 4 and 6 may be configured to receive and process natural language inputs. As a particular example, FIG. 1 shows a first user 8 in living room 2 providing natural language input to request the transfer of an instance of a computer game from one computing device to another. In another example, such a transfer may be performed programmatically without input from the user. For example, a computing device may utilize sensor data, such as audio and/or video data, for example received from a camera 10, to detect when the user moves to another room and is looking at or "engaged" with another device. Using this data, the computing device may automatically transfer the instance of the computer game to the other device.

As another example of a computing device action that may be requested with natural language input, FIG. 1 shows a second user 12 in living room 2 asking for information regarding future weather. Other information that may be requested of computing devices 4 and/or 6 may include but is not limited to personal calendar events, movie show times, and news. Computing devices 4 and/or 6 may receive and store messages and/or reminders to be delivered at an appropriate time. Using sensor data, the computing device(s) may track and/or communicate with one or more users or other entities. Further, in some examples, computing devices 4 and/or 6 may be utilized to control other computers, smart devices, and/or Internet of Things (IoT) devices. As an example, computing devices 4 and/or 6 may be configured to control elements in the living room 2, such as a television 14, speakers 16 of a music system, a gas fireplace 18, and/or motorized curtains 20.

Due to their proximity to users 8 and 12, computing devices 4 and 6 may hear the requests issued by both users. Were the operation of computing devices 4 and 6 not to be coordinated, both computing devices may respond to the same user. A disorienting user experience would result, as would unnecessary consumption of computational resources due to both computing devices servicing a common request. Accordingly, implementations are disclosed herein for coordinating the operation of multiple intelligent assistant computing devices in an environment, such that a single computing device is selected to respond to a user. Further, the selected computing device may evaluate a disengagement metric of the user against an adjustable threshold to selectively block or unblock subsequent responses to other users in the environment. As described in further detail below with reference to FIGS. 7-8B, a computing device may consider a variety of use conditions in selectively blocking subsequent responses to another user, including but not limited to an identity of the other user, one or more device settings of the computing device, and/or aspects of content available for presentation to the other user. By considering use conditions in this way, a computing device may provide a desired user experience by servicing a first user's requests while retaining the ability to respond to a second user under certain conditions.

In some examples, computing devices 4 and/or 6 may be operatively connected with each other and/or one or more other computing devices using a wired connection, or may employ a wireless connection via Wi-Fi, Bluetooth, or any other suitable wireless communication protocol. For example, computing devices 4 and/or 6 may be communicatively coupled to one or more other computing devices via a network. The network may take the form of a local area network (LAN), wide area network (WAN), wired network, wireless network, personal area network, or a combination thereof, and may include the Internet. Additional details regarding components and computing aspects of computing devices 4 and 6 are described in more detail below with reference to FIG. 12.

Figure 7:
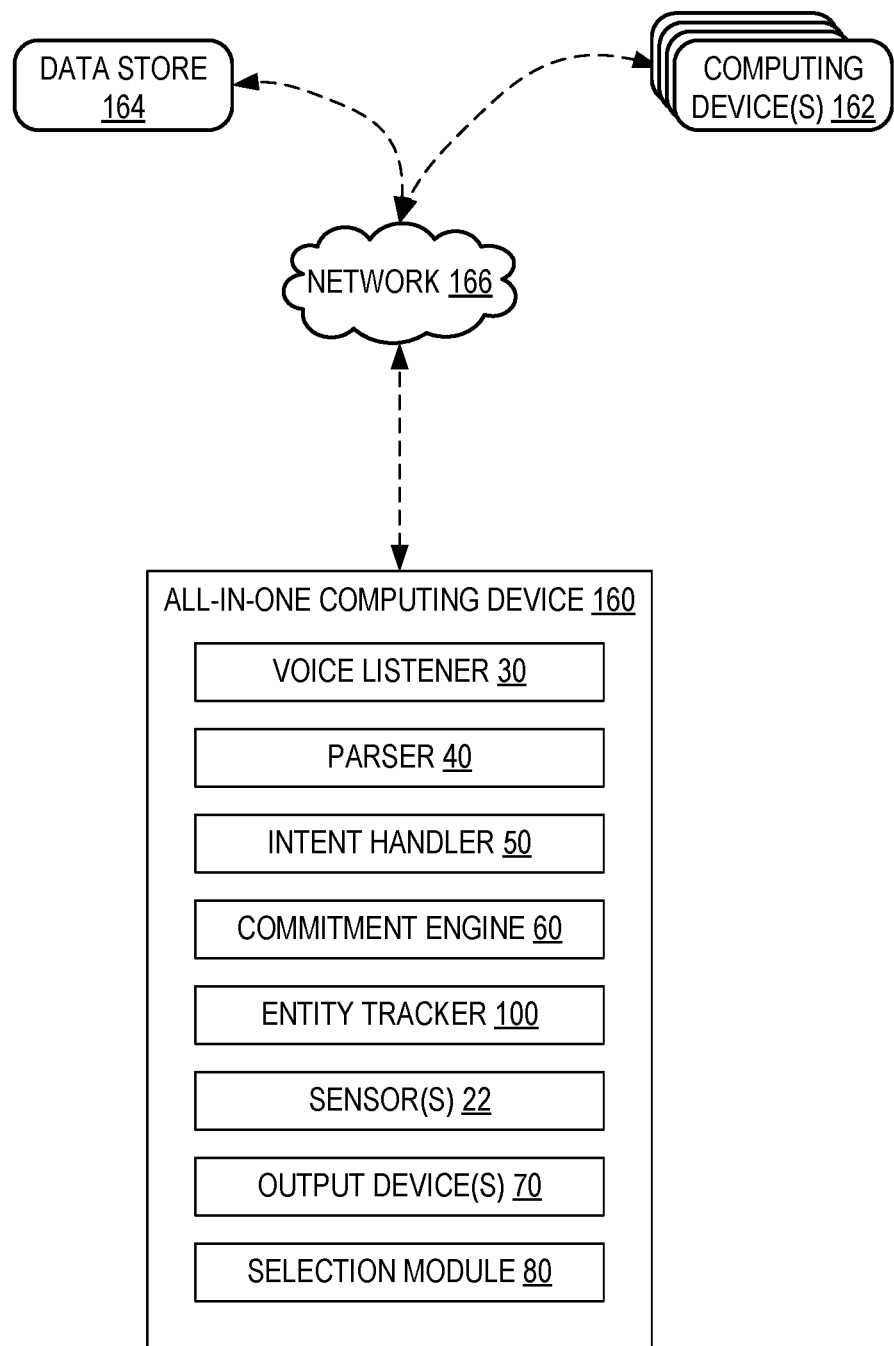
FIG. 7 schematically shows an all-in-one computing device that implements an intelligent assistant computer according to examples of the present disclosure.
Figure 10:
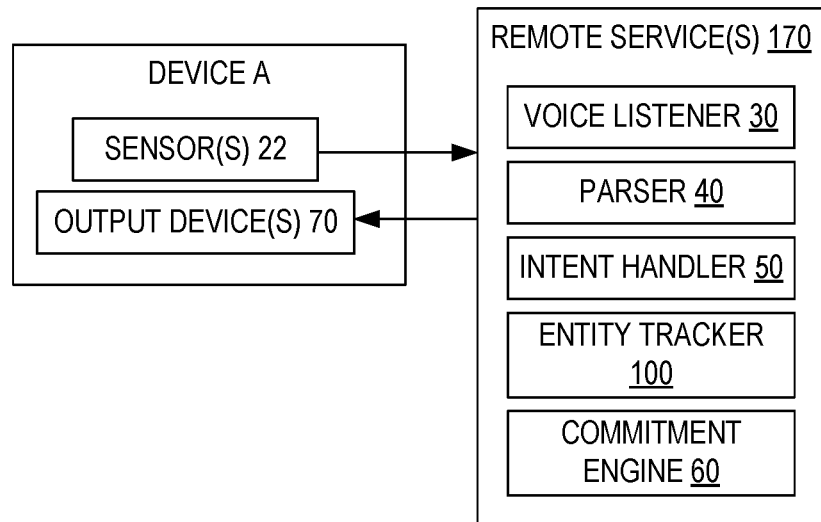
FIG. 10 schematically shows an example implementation in which one or more remote services perform functionality of the intelligent assistant computer according to examples of the present disclosure.
Figure 11:
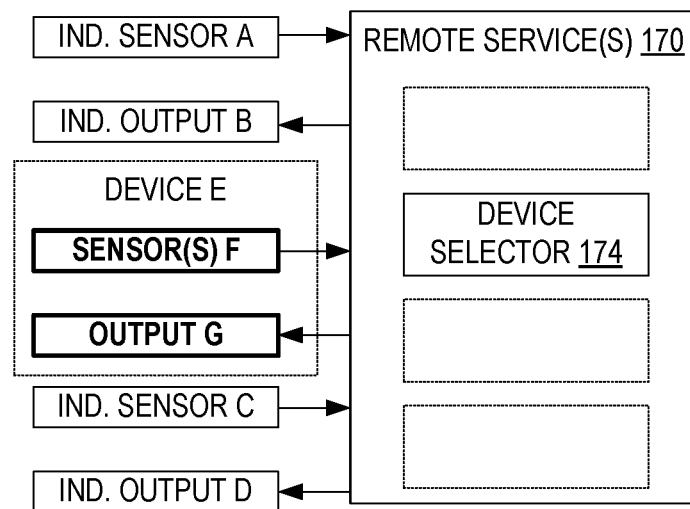
FIG. 11 schematically shows another example implementation in which one or more remote services perform functionality of intelligent assistant computer according to examples of the present disclosure.

It will be appreciated that computing devices 4 and 6 of FIG. 1 represent merely one example implementation of the intelligent assistant of the present disclosure. Additional example implementations across two or more devices are illustrated in FIGS. 7, 10, and 11 and described in more detail below.

Figure 2:
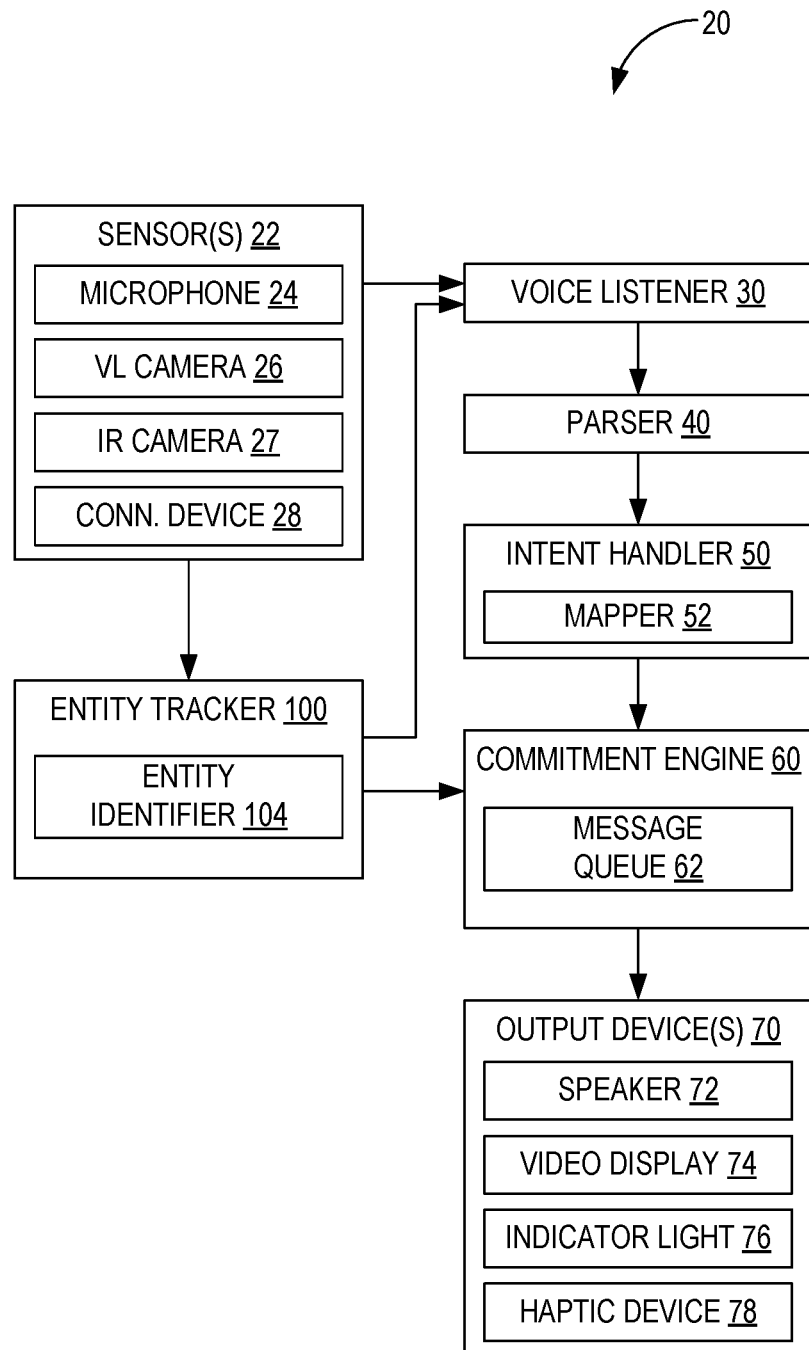
FIG. 2 schematically shows an example logical architecture for implementing an intelligent assistant computer according to an example of the present disclosure.

FIG. 2 shows an example logical architecture for implementing an intelligent assistant computer 20 capable of recognizing and responding to natural language inputs according to examples of the present disclosure. As described in more detail below, in various examples the system 20 may be implemented in a single computing device, across two or more devices, in a cloud-supported network, and in combinations of the foregoing.

In this example the intelligent assistant computer 20 includes at least one sensor 22, an entity tracker 100, a voice listener 30, a parser 40, an intent handler 50, a commitment engine 60, and at least one output device 70. In some examples the sensors 22 may include one or more microphones 24, visible light cameras 26, infrared cameras 27, and connectivity devices 28, such as Wi-Fi or Bluetooth modules. In some examples sensor(s) 22 may comprise stereoscopic and/or depth cameras, head trackers, eye trackers, accelerometers, gyroscopes, gaze detection devices, electric-field sensing componentry, GPS or other location tracking devices, temperature sensors, device state sensors, and/or any other suitable sensor.

The entity tracker 100 is configured to detect entities and their activities, including people, animals, or other living things, as well as non-living objects. Entity tracker 100 includes an entity identifier 104 that is configured to recognize individual users and/or non-living objects. Voice listener 30 receives audio data and utilizes speech recognition functionality to translate spoken utterances into text. Voice listener 30 also may assign confidence value(s) to the translated text, and may perform speaker recognition to determine an identity of the person speaking, as well as assign probabilities to the accuracy of such identifications. Parser 40 analyzes text and confidence values received from voice listener 30 to derive user intentions and generate corresponding machine-executable language.

Intent handler 50 receives machine-executable language representing user intentions from the parser 40, and resolves missing and ambiguous information to generate commitments. Commitment engine 60 stores commitments from the intent handler 50. At a contextually appropriate time, the commitment engine may deliver one or more messages and/or execute one or more actions that are associated with one or more commitments. Commitment engine 60 may store messages in a message queue 62 or cause one or more output devices 70 to generate output. The output devices 70 may comprise one or more of speaker(s) 72, video display(s) 74, indicator light(s) 76, haptic device(s) 78, and/or other suitable output devices. In other examples, output devices 70 may comprise one or more other devices or systems, such as home lighting, thermostats, media programs, door locks, etc., that may be controlled via actions executed by the commitment engine 60.

In different examples the voice listener 30, parser 40, intent handler 50, commitment engine 60, and/or entity tracker 100 may be embodied in software that is stored in memory and executed by one or more processors of a computing device. In some implementations, specially programmed logic processors may be utilized to increase the computational efficiency and/or effectiveness of the intelligent assistant computer. Additional details regarding the components and computing aspects of computing devices that may store and execute these modules are described in more detail below with reference to FIG. 12.

With reference again to FIG. 2, in some examples the voice listener 30 and/or commitment engine 60 may receive context information including associated confidence values from entity tracker 100. As described in more detail below, entity tracker 100 may determine an identity, position, and/or current status of one or more entities within range of one or more sensors, and may output such information to one or more other modules, such as voice listener 30, commitment engine 60, etc. In some examples, entity tracker 100 may interpret and evaluate sensor data received from one or more sensors, and may output context information based on the sensor data. Context information may include the entity tracker's guesses/predictions as to the identity, position, and/or status of one or more detected entities based on received sensor data. In some examples, the guesses/predictions may additionally include a confidence value defining the statistical likelihood that the information is accurate.

Figure 3:
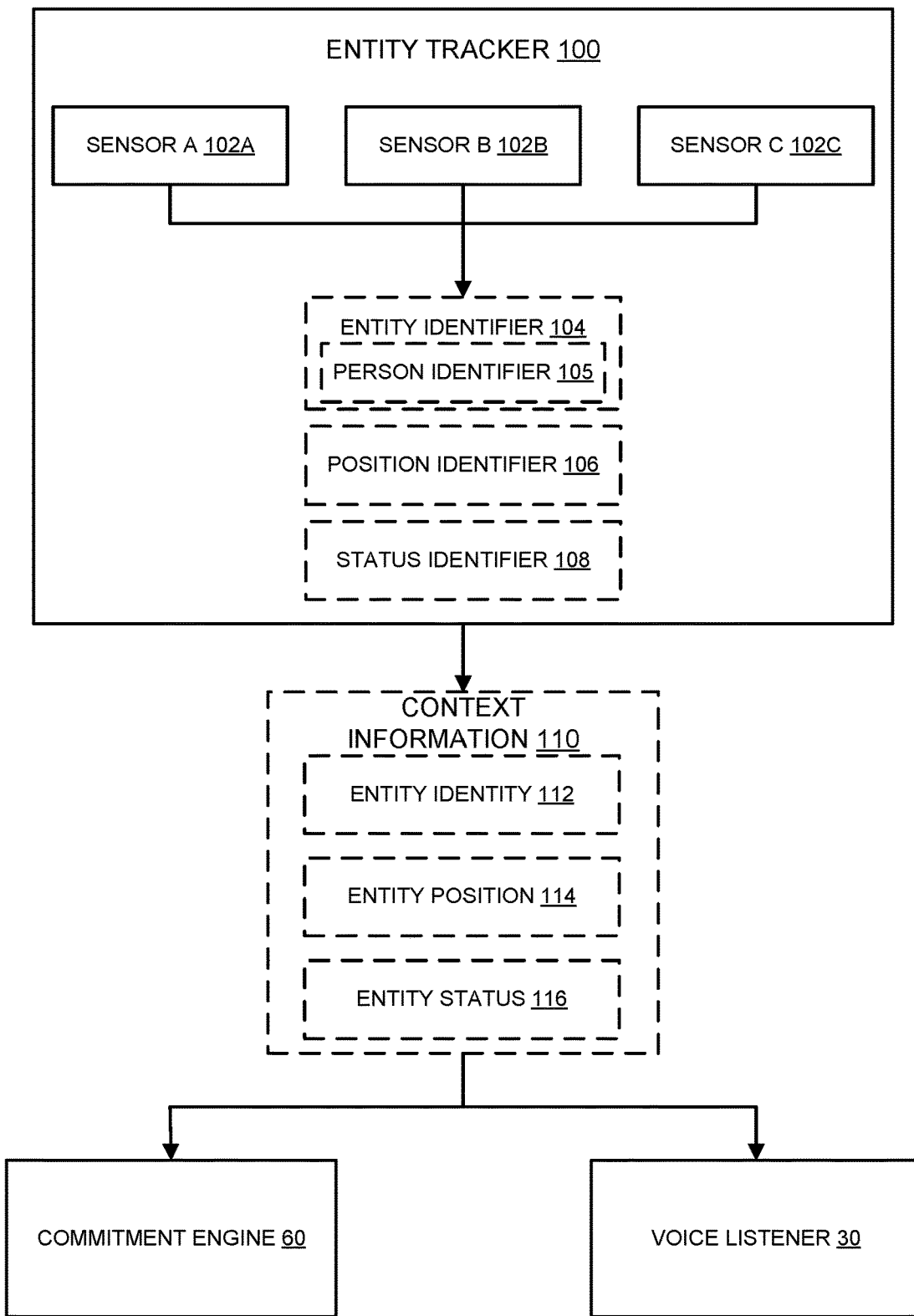
FIG. 3 schematically shows an entity tracker that may determine an identity, position, and/or current status of one or more entities according to examples of the present disclosure.

FIG. 3 schematically illustrates an example entity tracker 100 that may comprise a component of the intelligent assistant computer 20. Entity tracker 100 may be used to determine an identity, position, and/or current status of one or more entities within range of one or more sensors. Entity tracker 100 may output such information to one or more other modules of intelligent assistant computer 20, such as the commitment engine 60, voice listener 30, etc.

The word "entity" as used in the context of the entity tracker 100 may refer to people, animals, or other living things, as well as non-living objects. For example, the entity tracker may be configured to identify furniture, appliances, structures, landscape features, vehicles, and/or any other physical object, and determine the position/location and current status of such physical objects. In some cases, the entity tracker 100 may be configured to only identify people and not other living or non-living things. In such cases, the word "entity" may be synonymous with the word "person."

Entity tracker 100 receives sensor data from one or more sensors 102, such as sensor A 102A, sensor B 102B, and sensor C 102C, though it will be understood that an entity tracker may be used with any number and variety of suitable sensors. As examples, sensors usable with an entity tracker may include cameras (e.g., visible light cameras, UV cameras, IR cameras, depth cameras, thermal cameras), microphones, directional microphone arrays, pressure sensors, thermometers, motion detectors, proximity sensors, accelerometers, global positioning satellite (GPS) receivers, magnetometers, radar systems, lidar systems, environmental monitoring devices (e.g., smoke detectors, carbon monoxide detectors), barometers, health monitoring devices (e.g., electrocardiographs, sphygmomanometers, electroencephalograms), automotive sensors (e.g., speedometers, odometers, tachometers, fuel sensors), and/or any other sensors or devices that collect and/or store information pertaining to the identity, position, and/or current status of one or more people or other entities. In some examples, the entity tracker 100 may occupy a common device housing with one or more of the plurality of sensors 102, and/or the entity tracker and its associated sensors may be distributed across multiple devices configured to communicate via one or more network communications interfaces (e.g., Wi-Fi adapters, Bluetooth interfaces).

As shown in the example of FIG. 3, entity tracker 100 may include an entity identifier 104, a person identifier 105, a position (location) identifier 106, and a status identifier 108. In some examples, the person identifier 105 may be a specialized component of the entity identifier 100 that is particularly optimized for recognizing people, as opposed to other creatures and non-living things. In other cases, the person identifier 105 may operate separately from the entity identifier 104, or the entity tracker 100 may not include a dedicated person identifier.

Depending on the specific implementation, any or all of the functions associated with the entity identifier, person identifier, position identifier, and status identifier may be performed by the individual sensors 102A-102C. Though the present description generally describes the entity tracker 100 as receiving data from sensors, this does not require that the entity identifier 104, as well as other modules of the entity tracker, must be implemented on a single computing device that is separate and distinct from the plurality of sensors associated with the entity tracker. Rather, functions of the entity tracker 100 may be distributed amongst the plurality of sensors, or other suitable devices. For example, rather than sending raw sensor data to the entity tracker, individual sensors may be configured to attempt to identify entities that they detect, and report this identification to the entity tracker 100, and/or other modules of intelligent assistant computer 20. Furthermore, to simplify descriptions below, the term "sensor" is sometimes used to describe not only the physical measurement device (e.g., microphone or camera), but also the various logic processors configured and/or programmed to interpret signals/data from the physical measurement devices. For example, a "microphone" may be used to refer to the device that translates acoustic energy to an electrical signal, the analog-to-digital converter that converts the electrical signal to digital data, the on-board application-specific-integrated-circuit that pre-processes the digital data, and the downstream modules described herein (e.g., entity tracker 100, entity identifier 104, voice listener 30, or parser 40). As such, reference to a generic "sensor" or a particular sensor (e.g., "microphone" or "camera") should not be construed to mean only the physical measurement device, but also the cooperating modules/engines, which can be distributed across one or more computers.

Each of the entity identifier 104, person identifier 105, position identifier 106, and status identifier 108 is configured to interpret and evaluate sensor data received from the plurality of sensors 102, and to output context information 110 based on the sensor data. Context information 110 may include the entity tracker's guesses/predictions as to an identity, position, and/or status of one or more detected entities based on received sensor data. As will be described in more detail below, each of the entity identifier 104, person identifier 105, position identifier 106, and status identifier 108 may output their predictions/identifications along with a confidence value.

The entity identifier 104, person identifier 105, position identifier 106, status identifier 108, and other processing modules described herein may utilize one or more machine-learning technologies. Non-limiting examples of such machine-learning technologies can include Feedforward Networks, Recurrent Neural Networks (RNN), Long short-term Memory (LSTM), Convolutional neural networks, Support-vector machines (SVM), and Decision Trees. The various identifiers, engines, and other processing blocks described herein may be trained via supervised and/or unsupervised learning utilizing these, or any other appropriate, machine learning technologies to make the described assessments, decisions, identifications, etc. It should be understood, however, that this description is not intended to put forth new technologies for making such assessments, decisions, identifications, etc. Instead, this description is intended to manage computational resources, and as such, is meant to be compatible with any type of processing module.

The entity identifier 104 may output an entity identity 112 of a detected entity, and such entity identity may have any suitable degree of specificity. In other words, based on received sensor data, the entity tracker 100 may predict the identity of a given entity, and output such information as entity identity 112. For example, the entity identifier 104 may report that a particular entity is a piece of furniture, a dog, a human male, etc. Additionally, or alternatively, the entity identifier 104 may report that a particular entity is an oven with a particular model number; a pet dog with a specific name and breed; an owner or known user of intelligent assistant computer 20, with the owner/known user having a particular name and profile; etc. In some examples, the degree of specificity with which the entity identifier 104 identifies/classifies detected entities may depend on one or more of user preferences and sensor limitations.

When applied to people, the entity tracker 100 may in some cases collect information about individuals whom it is unable to identify by name. For example, the entity identifier 104 may record images of a person's face, and associate these images with recorded audio of the person's voice. Should the person subsequently speak to or otherwise address the intelligent assistant computer 20, the entity tracker 100 will then have at least some information regarding with whom the intelligent assistant computer is interacting. In some examples, the intelligent assistant computer 20 could also prompt the person to state their name, so as to more easily identify the person in the future.

In some examples, the intelligent assistant computer 20 may utilize a person's identity to customize a user interface for the person. In one example, a user may be identified who has limited visual capabilities. In this example and based on this identification, a display of the intelligent assistant computer 20 (or other device with which the user is interacting) may be modified to display larger text, or to provide a voice-only interface.

The position identifier 106 may be configured to output an entity position (i.e., location) 114 of a detected entity. In other words, the position identifier 106 may predict the current position of a given entity based on collected sensor data, and output such information as entity position 114. As with the entity identity 112, the entity position 114 may have any suitable level of detail, and this level of detail may vary with user preferences and/or sensor limitations. For example, the position identifier 106 may report that a detected entity has a two-dimensional position defined on a plane such as a floor or wall. Additionally, or alternatively, the reported entity position 114 may comprise a three-dimensional position of a detected entity within a real world, three-dimensional environment. In some examples an entity position 114 may comprise a GPS position, a location within a mapping coordinate system, etc.

The reported entity position 114 for a detected entity may correspond to the entity's geometric center, a particular part of the entity that is classified as being important (e.g., the head of a human), a series of boundaries defining the borders of the entity in three-dimensional space, etc. The position identifier 106 may further calculate one or more additional parameters describing the position and/or orientation of a detected entity, such as a pitch, roll, and/or yaw parameter. In other words, the reported position of a detected entity may have any number of degrees-of-freedom, and may include any number of coordinates defining the position of the entity in an environment. In some examples, an entity position 114 of a detected entity may be reported even if the entity tracker 100 is unable to identify the entity, and/or determine the current status of the entity.

Status identifier 108 may be configured to output an entity status 116 of a detected entity. In other words, the entity tracker 100 may be configured to predict the current status of a given entity based on received sensor data, and output such information as entity status 116. "Entity status" can refer to virtually any measurable or classifiable property, activity, or behavior of a given entity. For example, when applied to a person, the entity status of the person can indicate a posture of the person (e.g., standing, sitting, laying down), a speed at which the person is walking/running, a current activity of the person (e.g., sleeping, watching TV, working, playing a game, swimming, talking on the phone), a current mood of the person (e.g., by evaluating the person's facial expression or tone of voice), biological/physiological parameters of the person (e.g., the person's heart rate, respiration rate, oxygen saturation, body temperature, neurological activity), whether the person has any current or upcoming calendar events/appointments, etc. "Entity status" can refer to additional/alternative properties or behaviors when applied to other creatures or non-living objects, such as a current temperature of an oven or kitchen sink, whether a device (e.g., television, lamp, microwave) is powered on, whether a door is open, etc.

In some examples, the status identifier 108 may use sensor data to calculate a variety of different biological/physiological parameters of a human. This may be done in a variety of suitable ways. For example, the entity tracker 100 may be configured to interface with an optical heart rate sensor, a pulse oximeter, a sphygmomanometer, electrocardiograph, etc. Additionally or alternatively, the status identifier 108 may be configured to interpret data from one or more cameras and/or other sensors in an environment, and process the data in order to calculate a human's heart rate, respiration rate, oxygen saturation, etc. For example, the status identifier 108 may be configured to utilize Eulerian magnification and/or similar techniques to amplify miniscule movements or changes captured by the cameras, thereby allowing the status identifier to visualize the flow of blood through a human's circulatory system and calculate associated physiological parameters. Such information can be used, for example, to determine when the person is asleep, working out, in distress, experiencing health problems, etc.

Upon determining one or more of the entity identity 112, entity position 114, and entity status 116, such information may be sent as context information 110 to any of a variety of external modules or devices, where it may be used in a variety of ways. For example, context information 110 may be used by commitment engine 60 to manage commitments and associated messages and notifications. In some examples, context information 110 may be used by commitment engine 60 to determine whether a particular message, notification, or commitment should be executed and/or presented to a user. Similarly, context information 110 may be utilized by voice listener 30 when interpreting human speech or activating functions in response to a keyword trigger.

As noted above, in some examples the entity tracker 100 may be implemented in a single computing device. In other examples, one or more functions of the entity tracker 100 may be distributed across multiple computing devices working cooperatively. For example, one or more of the entity identifier 104, person identifier 105, position identifier 106, and status identifier 108 may be implemented on different computing devices, while still collectively comprising an entity tracker configured to perform the functions described herein. As indicated above, any or all of the functions of the entity tracker may be performed by individual sensors 102. Further, in some examples entity tracker 100 may omit one or more of the entity identifier 104, person identifier 105, position identifier 106, and status identifier 108, and/or include one or more additional components not described herein, while still providing context information 110. Additional details regarding components and computing aspects that may be used to implement entity tracker 100 are described in more detail below with respect to FIG. 12.

Each of entity identity 112, entity position 114, and entity status 116 may take any suitable form. For example, each of the entity identity 112, position 114, and status 116 may take the form of a discrete data packet including a series of values and/or labels describing the information gathered by the entity tracker. Each of the entity identity 112, position 114, and status 116 may additionally include a confidence value defining a statistical likelihood that the information is accurate. For example, if the entity identifier 104 receives sensor data that strongly indicates that a particular entity is a human male named "John Smith," then entity identity 112 may include this information along with a corresponding relatively high confidence value, such as 90% confidence. If the sensor data is more ambiguous, then the confidence value included in entity identity 112 correspondingly may be relatively lower, such as 62%. In some examples, separate predictions may be assigned separate confidence values. For example, the entity identity 112 may indicate with 95% confidence that a particular entity is a human male, and indicate with a 70% confidence that the entity is John Smith. Such confidence values (or probabilities) may be utilized by a cost function in generating cost calculations for providing messages or other notifications to a user and/or performing action(s).

In some implementations, the entity tracker 100 may be configured to combine or fuse data from multiple sensors in order to output more accurate predictions. As an example, a camera may locate a person in a particular room. Based on the camera data, the entity tracker 100 may identify the person with a confidence value of 70%. However, the entity tracker 100 may additionally receive recorded speech from a microphone. Based on the recorded speech alone, the entity tracker 100 may identify the person with a 60% confidence value. By combining the data from the camera with the data from the microphone, the entity tracker 100 may identify the person with a higher confidence value than would be possible using the data from either sensor alone. For example, the entity tracker may determine that the recorded speech received from the microphone corresponds to lip movements of the person visible to the camera when the speech was received, and thereby conclude with relatively high confidence, such as 92%, that the person visible to the camera is the person speaking. In this manner, the entity tracker 100 may combine the confidence values of two or more predictions to identify a person with a combined, higher confidence value.

In some examples, data received from various sensors may be weighted differently depending upon a reliability of the sensor data. This can be especially relevant in situations where multiple sensors are outputting seemingly inconsistent data. In some examples, the reliability of a sensor's data may be based at least in part on the type of data generated by the sensor. For example, in some implementations a reliability of video data may be weighted higher than a reliability of audio data, as the presence of an entity on camera may be a better indicator of its identity, position, and/or status than recorded sounds that are presumed to originate from the entity. It will be appreciated that a reliability of sensor data is a different factor than a confidence value associated with a predicted accuracy of an instance of data. For example, several instances of video data may have different confidence values based on different contextual factors present at each instance. Each of these instances of video data, however, may be associated with a single reliability value for video data in general.

In one example, data from a camera may suggest that a particular person is in a kitchen with a 70% confidence value, such as via face recognition analysis. Data from a microphone may suggest with a 75% confidence value that the same person is in a nearby hallway, such as via voice recognition analysis. Even though the instance of microphone data carries a higher confidence value, the entity tracker 100 may output a prediction that the person is in the kitchen based on a higher reliability of the camera data as compared to a lower reliability of the microphone data. In this manner and in some examples, different reliability values for different sensor data may be used along with confidence values to reconcile conflicting sensor data and determine an identity, position, and/or status of an entity.

Additionally, or alternatively, more weight may be given to sensors that have higher precision, more processing power or otherwise greater capabilities. For example, a professional-grade video camera may have a significantly improved lens, image sensor, and digital image processing capabilities as compared to a basic webcam found in a laptop. Accordingly, a higher weight/reliability value may be given to video data received from the professional-grade camera as compared to the webcam, as such data is likely to be more accurate.

Figure 4:
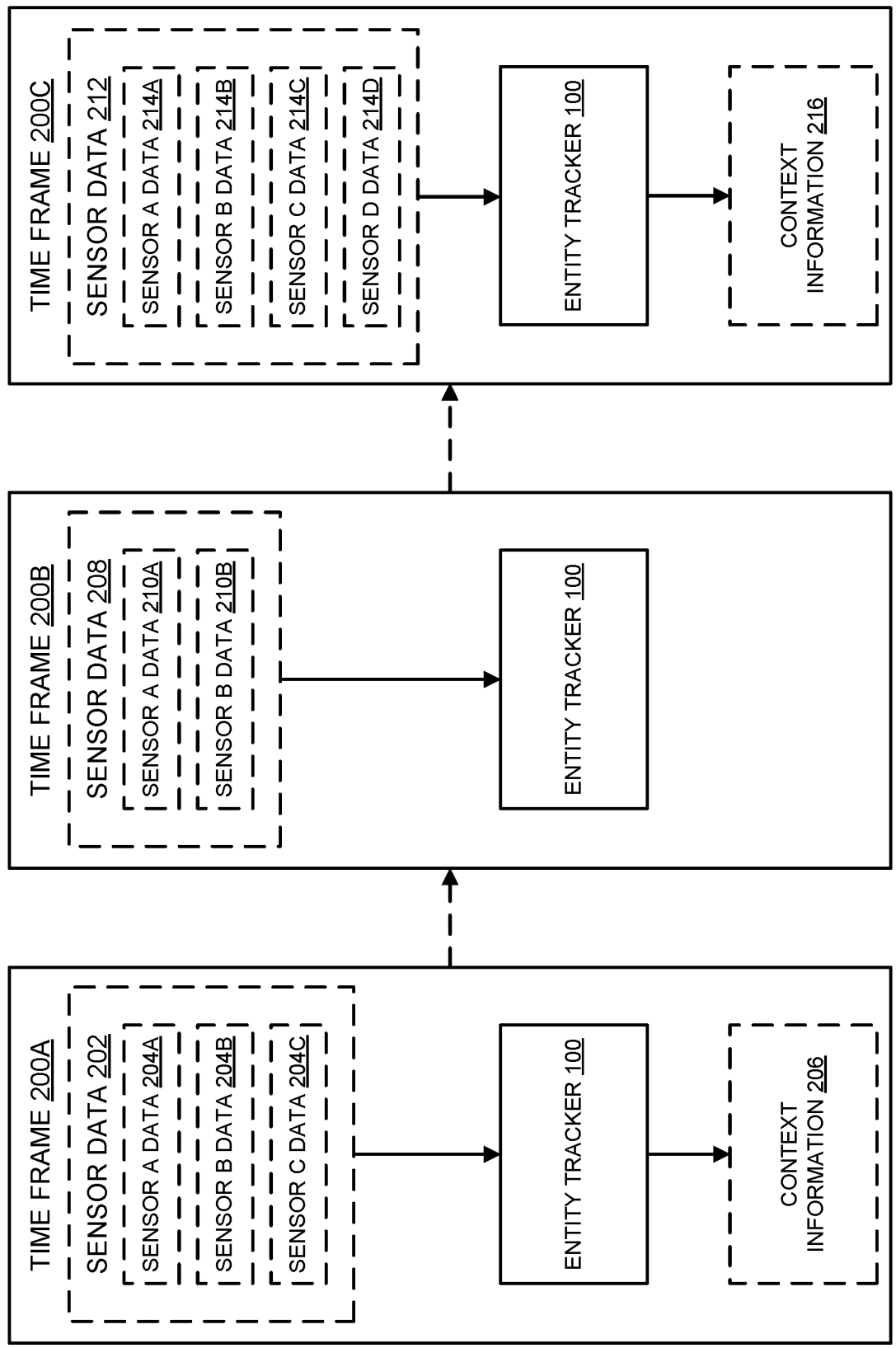
FIG. 4 schematically shows an entity tracker receiving and interpreting sensor data over multiple time frames according to examples of the present disclosure.

With reference now to FIG. 4, in some examples, individual sensors used with the entity tracker 100 may output data with a different frequency than other sensors used with the entity tracker. Similarly, sensors used with the entity tracker 100 may output data with a different frequency than the frequency with which the entity tracker evaluates the data and outputs context information. In the example of FIG. 4, entity tracker 100 may receive and interpret sensor data over multiple time frames 200A, 200B, and 200C. A single time frame may represent any suitable length of time, such as $\frac{1}{30}^{th}$ sec., $\frac{1}{60}^{th}$ sec., etc.

In this example, during time frame 200A entity tracker 100 receives a set of sensor data 202 including sensor A data 204A, sensor B data 204B, and sensor C data 204C. Such sensor data is interpreted by entity tracker 100 and transformed into context information 206, which may be used to determine an identity, position, and/or status of one or more detected entities as described above. During time frame 200B, entity tracker 100 receives sensor data 208, including sensor A data 210A and sensor B data 210B. Entity tracker 100 does not receive data from sensor C during time frame 200B, as sensor C outputs data at a different frequency than sensors A and B. Similarly, entity tracker 100 does not output context information during time frame 200B, as the entity tracker outputs context information at a different frequency than sensors A and B.

During time frame 200C, entity tracker 100 receives sensor data 212, including sensor A data 214A, sensor B data 214B, sensor C data 214C, and sensor D data 214D. Entity tracker 100 also outputs context information 216 during time frame 200C, which may be based on any or all of the sensor data received by the entity tracker since context information was last output in time frame 200A. In other words, context information 216 may be based at least in part on sensor data 208 as well as sensor data 212. In some examples, context information 216 may be based at least in part on sensor data 202 and sensor data 208, as well as sensor data 212.

As shown in FIG. 4, after the entity tracker 100 receives data from a particular sensor, multiple time frames may pass before the entity tracker receives more data from the same sensor. During these multiple time frames, entity tracker 100 may output context information. Similarly, the usefulness of data received from a particular sensor may vary from time frame to time frame. For example, at a first time frame the entity tracker 100 may receive audio data of a particular person speaking via a microphone, and accordingly identify an entity position 114 of the person with a relatively high confidence value. In subsequent time frames, the person may remain at the identified position, but also may have stopped speaking since the first time frame. In this case, the absence of useful data from the microphone may not be a reliable indicator of the absence of the person. Similar issues can arise with other types of sensors. For example, a camera may lose track of a person if he covers his face, or is occluded by an obstacle, such as another person or a moving object. In this case, though current camera data may not suggest the presence of the person, prior instances of camera data may suggest that the person is still located at the previously identified position. In general, while sensor data may reliably indicate the presence of an entity, such data may be less reliable in suggesting the absence of an entity.

Accordingly, the entity tracker 100 may utilize one or more confidence decay functions, which in different examples may be defined by the entity tracker and/or by the sensors themselves. A confidence decay function may be applied to sensor data to reduce the entity tracker's confidence in the data from a particular sensor as time passes since that sensor last positively detected an entity. As an example, after a sensor detects an entity at a particular location, the entity tracker 100 may report context information 110 indicating that the entity is at the location with relatively high confidence. If after one or more time frames the sensor no longer detects the entity at the location, and unless it subsequently gathers contradictory evidence, the entity tracker 100 still may report that the entity is at the location, though with a somewhat lower confidence. As time continues to pass since the sensor last detected the entity at the location, it becomes progressively less likely that the entity is still at the location. Accordingly, the entity tracker 100 may utilize the confidence decay function to progressively decrease the confidence value of its reported context information 110, eventually reaching 0% confidence if no additional sensors detect the entity.

In some cases, different confidence decay functions may be utilized with different sensors and sensor types. A selection of a particular decay function may depend at least in part on particular properties of a sensor. For example, confidence values associated with data from a video camera may decay more rapidly than confidence values associated with data from a microphone, as absence of an entity in a video frame is a more reliable indicator of the entity's absence than silence recorded by a microphone.

Figure 5:
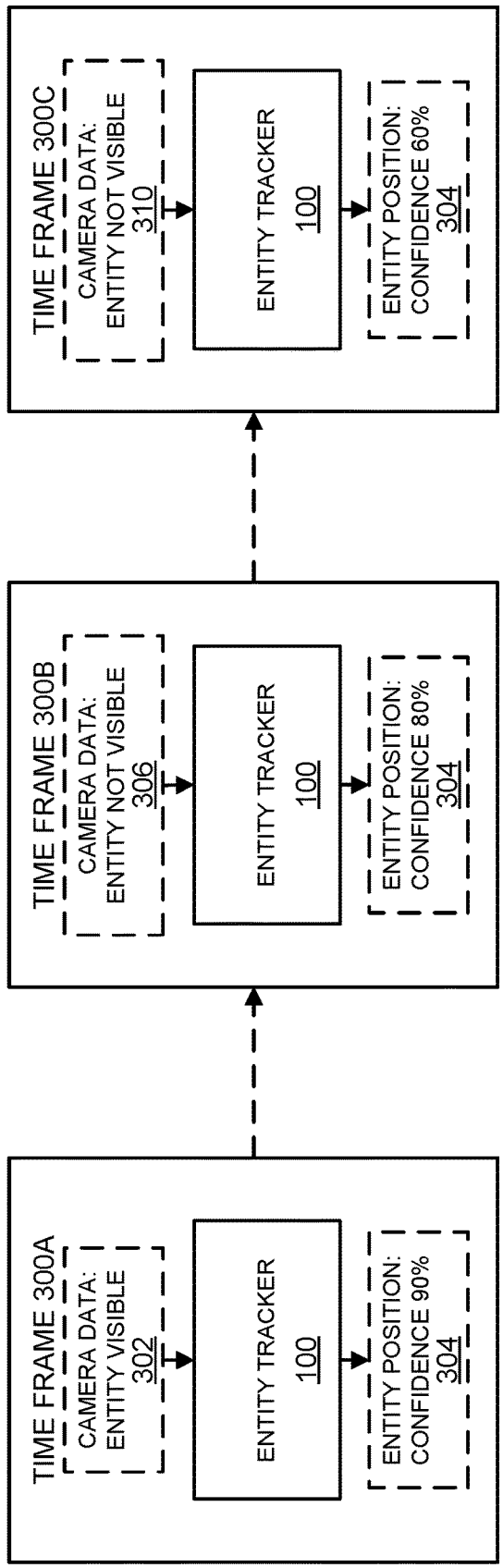
FIG. 5 schematically shows an example of sensor confidence decay over time via an entity tracker according to an example of the present disclosure.

One example of sensor confidence decay is schematically illustrated in FIG. 5, which shows entity tracker 100 receiving sensor data during three different time frames 300A, 300B, and 300C. During time frame 300A, entity tracker 100 receives camera data 302 in which an entity is visible in the frame. Based on this data, the entity tracker 100 reports the entity position 304 with a 90% confidence value. In time frame 300B, entity tracker 100 receives camera data 306 in which the entity is no longer visible in the frame. However, it is possible that the entity has not moved, and has merely become occluded, or otherwise undetectable to the camera. Accordingly, entity tracker 100 reports the same entity position 304, but with a lower confidence value of 80%.

Finally, in time frame 300C entity tracker 100 receives camera data 310 indicating that the entity is still not visible in the frame. As time has passed, it has grown less likely that the entity is still in the same position. Accordingly, the entity tracker 100 reports the same entity position 304 with a still lower confidence value of 60%.

In some examples, variable reliability of sensor data may be at least partially addressed by making use of data filtering techniques. In some examples, a Kalman filter may be utilized to filter sensor data. A Kalman filter is a mathematical function that may combine multiple uncertain measurements and output a prediction with more confidence than would be possible using any individual measurement. Each measurement input to the Kalman filter is given a weight based on the measurement's perceived reliability. Kalman filters operate in a two-step process, including a prediction step and an update step. During the prediction step, the filter outputs a prediction based on recent weighted measurements. During the update step, the filter compares its prediction to an actual observed value or state, and dynamically adjusts the weighting applied to each measurement so as to output more accurate predictions.

In some examples, entity tracker 100 may comprise a Kalman filter that combines data from a variety of sensors to compensate for lower sensor reliability, such as when sensor confidence values have decayed over time since the last positive detection. In some examples, entity tracker 100 may apply a Kalman filter to sensor data when one or more sensor confidence values are below a predetermined threshold. In an example scenario, image data from a camera may be analyzed using face detection techniques to reliably detect a person in a particular room. In response, the entity tracker 100 may report with high confidence that the person is located in the room.

In subsequent time frames, the camera may no longer be able to capture and/or positively recognize the person's face in the room. For example, the person's face may become occluded, or the camera may transmit data with a much lower frequency than the entity tracker 100 outputs context information 110. If the entity tracker 100 relied exclusively on data from the camera, then the confidence value of its reported position of the person would gradually decrease until the next positive detection. However and in some examples, data from the camera may be supplemented with data from other sensors. For example, during the subsequent time frames a microphone may report that it hears the person's voice in the room, or another sensor may report that it can detect the presence of the person's portable computing device in the room. In such cases, this data may be assigned weights by the Kalman filter, and may be used to predict the person's current location with more confidence than would be possible if only the camera data were used.

In some cases, detection of people and/or other entities in an environment can become more complicated when sensor data is contaminated by background information. Such background information may compromise the confidence with which the entity tracker 100 reports entity identity 112, position 114, and/or status 116. For example, the intelligent assistant computer 20 may need to determine the identity of a person who is speaking in order to appropriately respond to a query or command. Such a determination can be difficult when multiple people are speaking at the same time, a television is playing, loud machinery is operating, etc.

Accordingly, the entity tracker 100 may use a variety of audio processing techniques to more confidently identify a particular active participant who is engaged in a conversation with other people and/or with the intelligent assistant computer 20. As an example, the entity tracker 100 may implement a voice activity detection (VAD) engine that may distinguish human voices from environmental noise, and identify the presence or absence of human speech.

General-purpose VAD engines may be used for the purpose of classifying a particular segment of audio as including either speech or non-speech, with a corresponding confidence value. An entity tracker 100 also may utilize a speaker recognition engine to match a particular audio segment with a particular person. As more speech is received, the speaker recognition engine may be progressively tailored to classify the audio as including speech from a particular conversation participant, or not including speech from the particular conversation participant. In this manner, the entity tracker 100 may recognize speech from one or more particular persons/conversation participants.

Training of a speaker recognition engine may occur any time the entity tracker 100 has confidently identified a particular person and recorded audio that can be confidently attributed to that person. For example, using camera data, the entity tracker 100 may identify a particular person and determine that the person's lips are moving. The entity tracker 100 may simultaneously receive audio from a microphone that can be safely assumed to include speech from the identified person. Accordingly, the received audio can be used to retrain the speaker recognition engine to more specifically recognize the identified person's voice.

In some cases, such retraining may occur only when the person has been identified with a high confidence value (e.g., via accurate facial recognition or any other method), such as a confidence value exceeding a predetermined threshold, and when the entity tracker 100 has received an audio recording of the person's voice having high volume/amplitude and a high signal-to-noise ratio (S/N). Using this technique, the entity tracker 100 may accumulate a variety of person-specific voice models, allowing the entity tracker to more consistently identify speech from particular people and ignore background noise.

Figure 6:
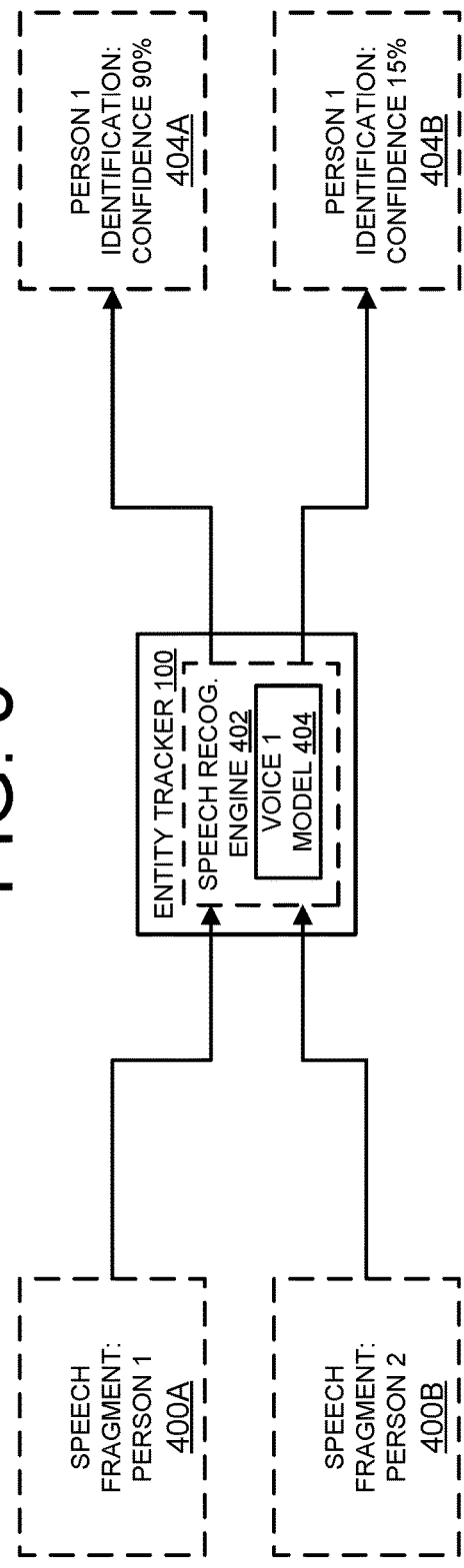
FIG. 6 schematically shows an example of using a trained voice recognition engine to recognize a person's speech according to examples of the present disclosure.

With reference now to FIG. 6, an example of using a trained speech recognition engine to recognize speech from a particular person is schematically illustrated. In this example, entity tracker 100 receives two speech fragments 400A and 400B. Speech fragment 400A includes recorded speech of a person 1, and speech fragment 400B includes recorded speech of a person 2. Entity tracker 100 includes a speech recognition engine 402 that has been specifically trained to recognize speech from person 1 using a voice 1 model 404, as described above. Voice 1 model 404 may be applied to each of speech fragment 400A and speech fragment 400B as they are received by the entity tracker 100.

Upon processing the speech fragments, the entity tracker 100 outputs a prediction of the likelihood that each speech fragment corresponds to person 1. As shown, for speech fragment 400A, the entity tracker outputs a person 1 identification 404A with a 90% confidence value, indicating that the speech fragment likely includes speech from person 1. For speech fragment 400B, the entity tracker outputs a person 1 identification 404B with a 15% confidence value, indicating that speech fragment 400B likely does not include speech from person 1.

In some examples, an entity tracker 100 may be configured to identify background noise present in an environment, and use audio processing techniques to subtract such background noise from received audio data. For example, a particular device in a person's home may be playing background audio, such as music or television/movie dialogue. Various microphone-equipped devices in the person's home may record such audio. Where such microphone-equipped devices include the intelligent assistant computer 20 and/or provide audio data to the entity tracker 100, such background audio may compromise the ability of the system to identify, interpret and/or respond to human questions or commands.

Accordingly and in some examples, the device playing the background audio and/or another microphone-equipped device recording the background audio may send the captured audio signal to the entity tracker 100. In this manner, the entity tracker 100 may subtract the background audio from the audio signal received from the microphone-equipped devices. In some examples, the subtraction of the background audio signal from the recorded audio data may be performed by the device(s) that capture the audio data, or by associated audio-processing components, prior to sending the audio data to the entity tracker 100.

Additionally or alternatively, devices and/or the entity tracker 100 may be trained to recognize particular sources of background noise (e.g., from an air vent or refrigerator), and automatically ignore waveforms corresponding to such noise in recorded audio. In some examples, an entity tracker 100 may include one or more audio-recognition models trained specifically to recognize background noise. For example, audio from various noise databases may be run through unsupervised learning algorithms in order to more consistently recognize such noise. By allowing the entity tracker 100 to recognize irrelevant background noise, the ability of the entity tracker to recognize relevant human speech and other sounds may be improved. In some implementations, positional knowledge of a sound source may be used to focus listening from a directional microphone array.

With reference now to FIGS. 7, 10, and 11, additional example implementations of intelligent assistant computer 20 in a single computing device and across multiple computing devices are illustrated. Additional details regarding components and computing aspects of computing devices illustrated in FIGS. 7, 10, and 11 are described below with reference to FIG. 12.

FIG. 7 shows an example of an all-in-one computing device 160 in which the components implementing intelligent assistant computer 20 are arranged together in a stand-alone device. In some examples, all-in-one computing device 160 may be communicatively coupled to one or more other computing devices 162 via a network 166. In some examples, all-in-one computing device 160 may be communicatively coupled to a data store 164 that may store a variety of data, such as user profile data. All-in-one computing device 160 includes at least one sensor 22, voice listener 30, parser 40, intent handler 50, commitment engine 60, entity tracker 100, and at least one output device 70. Sensor(s) 22 include at least one microphone to receive natural language inputs from a user. In some examples one or more other types of sensor(s) 22 also may be included.

As described above, voice listener 30, parser 40, and intent handler 50 work in concert to convert natural language inputs into commitments that are executable by the all-in-one device 160. The commitment engine 60 stores such commitments in a commitment storage 626. The entity tracker 100 may provide context information to the commitment engine 60 and/or other modules. At a contextually appropriate time, the commitment engine 60 may execute a commitment and provide output, such as audio signals, to output device(s) 70.

In some scenarios, multiple intelligent assistant computers may hear the same request spoken by a user, for example due to their placement in a common environment. As described above with reference to FIG. 1, it may be desirable in such scenarios to coordinate operation of the intelligent assistant computers such that a single assistant is selected to respond to the user's request, in order to avoid a disorienting user experience and unnecessary expenditure of computational resources that might result if multiple assistants were to respond to the same request. To this end, all-in-one computing device 160 may include a selection module 80 configured to determine whether to respond to a first user's request by comparing a self-selection score to one or more remote-selection scores from other intelligent assistant computers that also heard the same request. If the self-selection score is greater than the remote-selections score(s), all-in-one computing device 160 may respond to the user. Similarly, if a remote-selection score of another intelligent assistant computer is the greatest among the selection scores, that intelligent assistant may respond to the user. For scenarios in which one or more other users are also present and issue requests to all-in-one computing device 160, selection module 80 may further block subsequent responses to all of the other user(s) until a disengagement metric of the first user exceeds a blocking threshold. As described in further detail below with reference to FIGS. 8A-8B, the selection and response processes are configured so that a first user's requests are coherently serviced, while retaining the ability to respond to other users in appropriate contexts that do not interrupt the first user's computing device interactions. Further, in other examples at least a portion, and in some examples all, of the functions provided by selection module 80 may be implemented on one or more remote computing devices communicatively coupled with all-in-one device 160, as described below with reference to FIG. 11.

To illustrate the device selection described above, FIGS. 8A-8B show a flowchart illustrating a method 500 of selectively responding, at an intelligent assistant, to a user in a multi-user, multi-assistant environment. At least a portion of method 500 may be implemented by selection module 80 of all-in-one computing device 160, for example, and further may be implemented by similarly-configured selection modules provided on one or more other computing devices that interact with the all-in-one computing device. In other examples, at least a portion of method 500 may be implemented on one or more computing devices remote from a computing device or audio output device that provides a response to a user.

At 502, method 500 includes recognizing, at the intelligent assistant, another intelligent assistant located in a same environment as the intelligent assistant. As one example with reference to FIG. 1, computing device 4 may recognize computing device 6 in living room 2. Any suitable method may be employed to recognize another intelligent assistant. For example, the intelligent assistants may be part of the same network and/or registered with one another or a central service, and location/presence of the various intelligent assistants may be shared with one another. As another example, and with reference to FIG. 2, one or more of sensors 22 may be used to recognize the other intelligent assistant.

At 504, method 500 includes recording speech spoken by a first user. The speech may include any suitable utterance that can be recognized and used to trigger the performance of a computing device action by the intelligent assistant. As examples, the utterance may include a request for information or a change in application state. In some scenarios, the speech may include a keyword directing the intelligent assistant to analyze the speech spoken by the first user. The speech may be recorded in any suitable manner, such as by microphone 24 (FIG. 2) and/or one or more microphones located remotely from the intelligent assistant. As used herein, "record" includes translating sound waves into a digital format understandable by computers, and only optionally includes saving the digitized audio.

At 506, method 500 includes determining a self-selection score for the first user based on speech spoken by the first user. The speech on which determination of the self-selection score is based may be the same as, or different from, the speech recorded at 504. Generally, the selection scores described herein may represent the suitability of a corresponding intelligent assistant for responding to a user, and may consider the quality of recorded speech and/or confidence regarding aspects of recorded speech in determining such suitability. As specific examples, score determination may include evaluating one or more of (1) the amplitude of recorded speech, (2) the signal-to-noise ratio (SNR) of recorded speech, (3) a keyword confidence value indicating a likelihood that the recorded speech includes a keyword or keyword phrase, and (4) a user identification confidence value indicating a likelihood that the user is a particular person—e.g., that the user's identity is a known identity.

In some examples, the amplitude and/or SNR values may be received with the recorded speech. In other examples with reference to FIG. 2, amplitude and/or SNR values may be determined by the voice listener 30 or other components of the intelligent assistant system 20. As described above, the keyword confidence value may be determined by the voice listener 30. Also as described above, the user identification confidence value may be determined by entity tracker 100. In some examples, the user uttering the speech may be identified by voice recognition as a known speaker or an unknown speaker, and assigned a corresponding level of confidence.

The SNR may be calculated for the recorded speech by comparing a signal level of a user's voice to a level of background noise. In some examples, the amplitude of the input may be used to determine a proximity of the user to a corresponding microphone. It will be appreciated that the metrics discussed in the present implementations are provided as examples and are not meant to be limiting.

In some examples, a selection score may be determined by combining the four metrics described above (amplitude, SNR, keyword/keyword phrase confidence, user ID confidence) into a single selection score, such as by averaging the metrics. In some examples and prior to combining, each of the metrics may be weighted by empirically-determined weights that reflect the accuracy of a metric in predicting the device/microphone and corresponding audio data stream that will provide the best user experience. In other examples, one or more of the metrics may be kept separate from others and compared to other values of the same metric as described below.

Selection score determination may account for alternative or additional information. As examples, image data (e.g., collected with camera 26 and/or 27, both of FIG. 2) capturing lip motion, an eye gaze, and/or a face of the first user, and/or output from one or more proximity sensors (e.g., image proximity sensors, acoustic proximity sensors) may be considered.

At 508, method 500 includes sending the self-selections score for the first user to the other intelligent assistant in the environment. The self-selection score may be sent via any suitable network connection—e.g., via a direct network connection to the other intelligent assistant, via one or more intermediate network devices (e.g., switch, router, hub), via one or more intermediate computing devices that perform at least a portion of method 500. As an example with reference to FIG. 7, the self-selection score may be sent via network 166.

At 510, method 500 includes receiving a remote-selection score for the first user from the other intelligent assistant. The remote-selection score may be received via any suitable network connection as described above. To ensure that the self and remote-selection scores correspond to the same user, each may be transmitted with an identity of the same user, which may be determined in accordance with the techniques described herein. Alternatively, for example if an identity of the user cannot be determined, data that may be approximately or substantially unique to the user may be transmitted with the selection scores as a proxy for identity. For example, characteristics (e.g., waveforms, spectral analyses, timing information) of the audio streams recorded at each intelligent assistant may be transmitted to the other, and/or characteristics of other data types (e.g., feature vectors of facial image data, body and/or gait analysis data).

At 512, method 500 includes comparing the self-selection score for the first user to the remote-selection score for the first user. The selection scores may be compared in any suitable manner. For implementations in which the selection scores comprise a single number, the comparison may include identifying the higher number. For implementations in which one or more metrics are separately maintained, the values determined by the intelligent assistants for those metrics may be compared individually or a vector comparison may be made where the individual values serve as different components of a vector. A weighting scheme may be applied in comparing individual metrics to determine which assistant ultimately produced the higher selection score.

As a particular example of comparing selection scores for three devices, with scores expressed as a percentage, the following scores may be determined for the audio data stream received from a microphone A of a mobile phone: 1) 90% (Amplitude); 2) 90% (SNR); 3) 30% (Keyword confidence); 4) 90% (Speaker ID). Scores for the audio data stream received from microphone B of a tablet computer may be: 1) 80% (Amplitude); 2) 80% (SNR); 3) 80% (Keyword confidence); 4) 80% (Speaker ID). Scores for the audio data stream received from the microphone C of an intelligent assistant device may be: 1) 92% (Amplitude); 2) 88% (SNR); 3) 90% (Keyword confidence); 4) 92% (Speaker ID).

In this example, the rankings of the 3 devices for each of the four metrics would be as follows:
- A. Amplitude—1. Intelligent assistant device; 2. Mobile phone; 3. Tablet computer.
- B. SNR—1. Mobile phone; 2. Intelligent assistant device; 3. Tablet computer.
- C. Keyword Confidence—1. Intelligent assistant device; 2. Tablet computer; 3. Mobile phone.
- D. Speaker ID—1. Intelligent assistant device; 2. Mobile phone; 3. Tablet computer.

Each device may be awarded points based on its ranking in each metric category. For example, a first place ranking=1 point, second place=2 points and third place=3 points. For each device, its points are totaled for the four metrics and averaged. The device (and corresponding data stream) with the lowest average point total may be selected for determining a response to the first user as described below. In the present example, the final point totals and rankings are: 1. Intelligent assistant device=>1.25; 2. Mobile phone=>2.0; 3. Tablet computer=>2.75. The data stream from the intelligent assistant device may be selected for determining the response. Based on the above ranking, the intelligent assistant device may be selected to receive the message(s) generated by commitment engine 60 (FIG. 7) as a result of the analysis.

At 514, method 500 includes determining whether the self-selection score is greater than or less than the remote-selection score. The determination is based on the comparison performed at 512. If it is determined that the self-selection score is less than the remote-selection score (LESS), method 500 proceeds to 556. If it is determined that the self-selection score is greater than the remote-selection score (GREATER), method 500 proceeds to 516. Any suitable approach may be used to break ties—for example, favoring a particular metric (e.g., amplitude) or defaulting to a particular intelligent assistant.

At 516, method 500 optionally includes determining a disengagement metric of the first user. Generally, the disengagement metric represents an extent to which the first user is, and/or will be as a predictive measure, disengaged from interaction with the intelligent assistant. By extension, the disengagement metric may be used to determine how disruptive providing a response to another user would be to the first user's interaction with the intelligent assistant. For example, the greater the disengagement metric—e.g., the more disengaged the first user—the less likely it is that providing a response to another user would disrupt the first user's interaction with the intelligent assistant. As described in further detail below, the disengagement metric may be compared to a threshold to determine conditions in which it is appropriate to respond to another user engaging the intelligent assistant, enabling both users' requests to be serviced in a non-disruptive manner.

The disengagement metric may be implemented as a numerical value, which may be calculated by an algorithm that takes one or more inputs. An audio stream including speech spoken by the first user may be evaluated in determining one or more inputs to calculate the disengagement metric for the first user, for example. In particular, a conversational context indicated by the audio stream may be evaluated, where the context may include the first user addressing the intelligent assistant. Another conversational context may indicate, by a lack of recorded speech, that the first user has ceased engaging the intelligent assistant. The algorithm used to calculate the disengagement metric may take a time since a last recorded speech from the use. For example, the disengagement metric may be gradually decreased according to the inverse of a time decay function that models the time decay of the user's engagement with the intelligent assistant—e.g., as more time passes in which the user does not address the intelligent assistant, it is considered increasingly likely that the user has ceased engaging the assistant, at least until a new conversation or request is started.

Alternative or additional data may be considered in determining the disengagement metric, including one or more of the data types described above used to determine selection scores. As additional examples, the disengagement metric may be raised as the first user disappears from image data, looks away from the intelligent assistant as determined from eye gaze data, and/or performs hand gestures directed away from the assistant. Further, as indicated at 518, the disengagement metric may be set to a maximum value responsive to an explicit command from the first user to disengage from the intelligent assistant (e.g., a command to end a current conversation, power down the assistant, place the assistant in an idle or standby state). Similarly, the first user may issue an explicit command to engage the intelligent assistant, which may lower (e.g., minimize) the disengagement metric.

As an inverse relationship may exist between a user's disengagement with the intelligent assistant and his or her engagement with the assistant, the approaches described herein for determining and evaluating a disengagement metric may be adapted to alternatively or additionally determine an engagement metric that represents a user's engagement with the assistant. For example, determination of one of the disengagement and engagement metrics may yield the other by computing the determined metric's inverse. For implementations in which the engagement metric is used, the blocking threshold described below may be adapted for comparison to the engagement metric (e.g., by reversing the directionality of comparison).

Figure 8A:
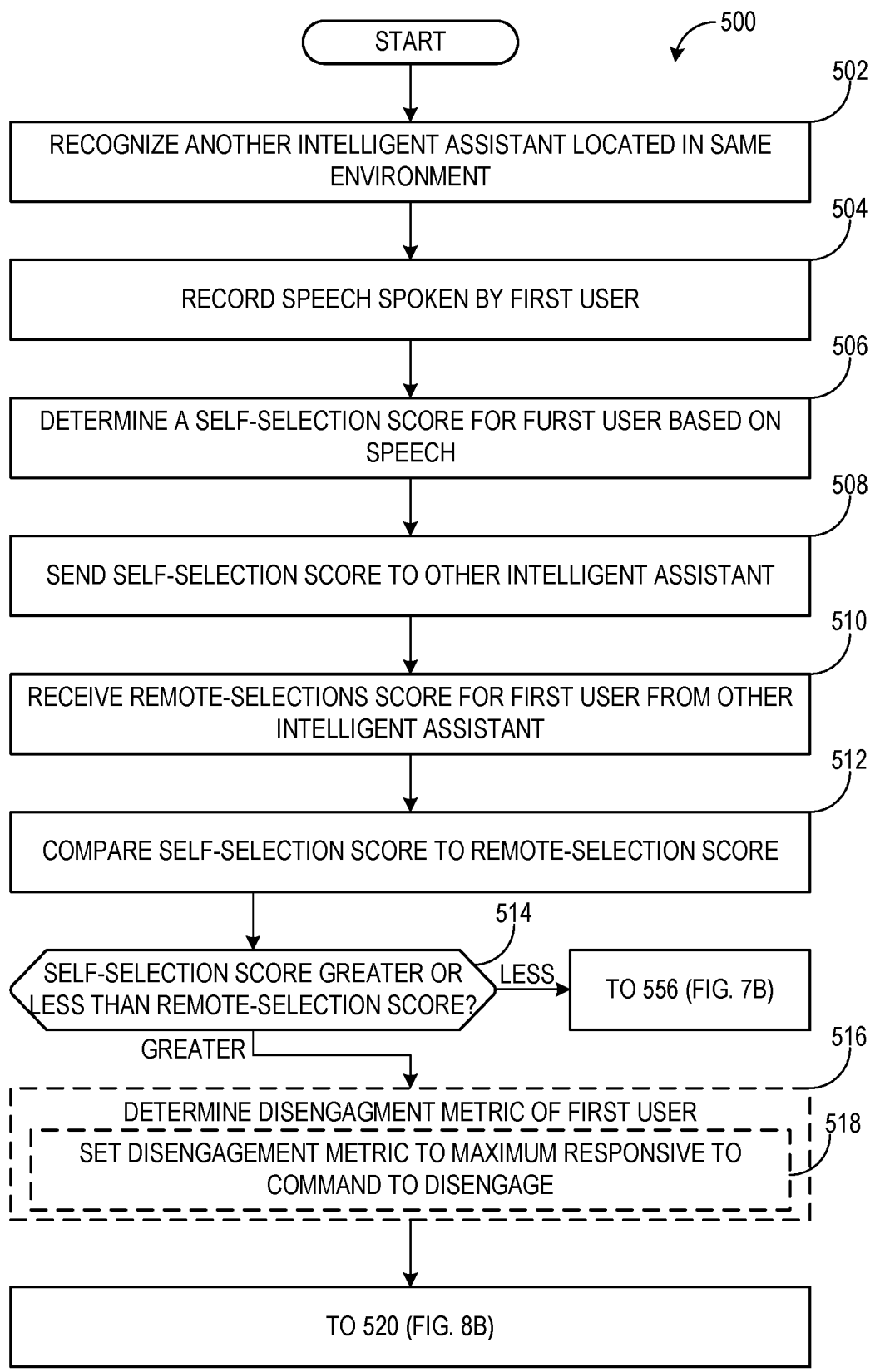
FIGS. 8A-8B show a flowchart illustrating a method of selectively responding, at an intelligent assistant, to a user in a multi-user, multi-assistant environment.
Figure 8B:
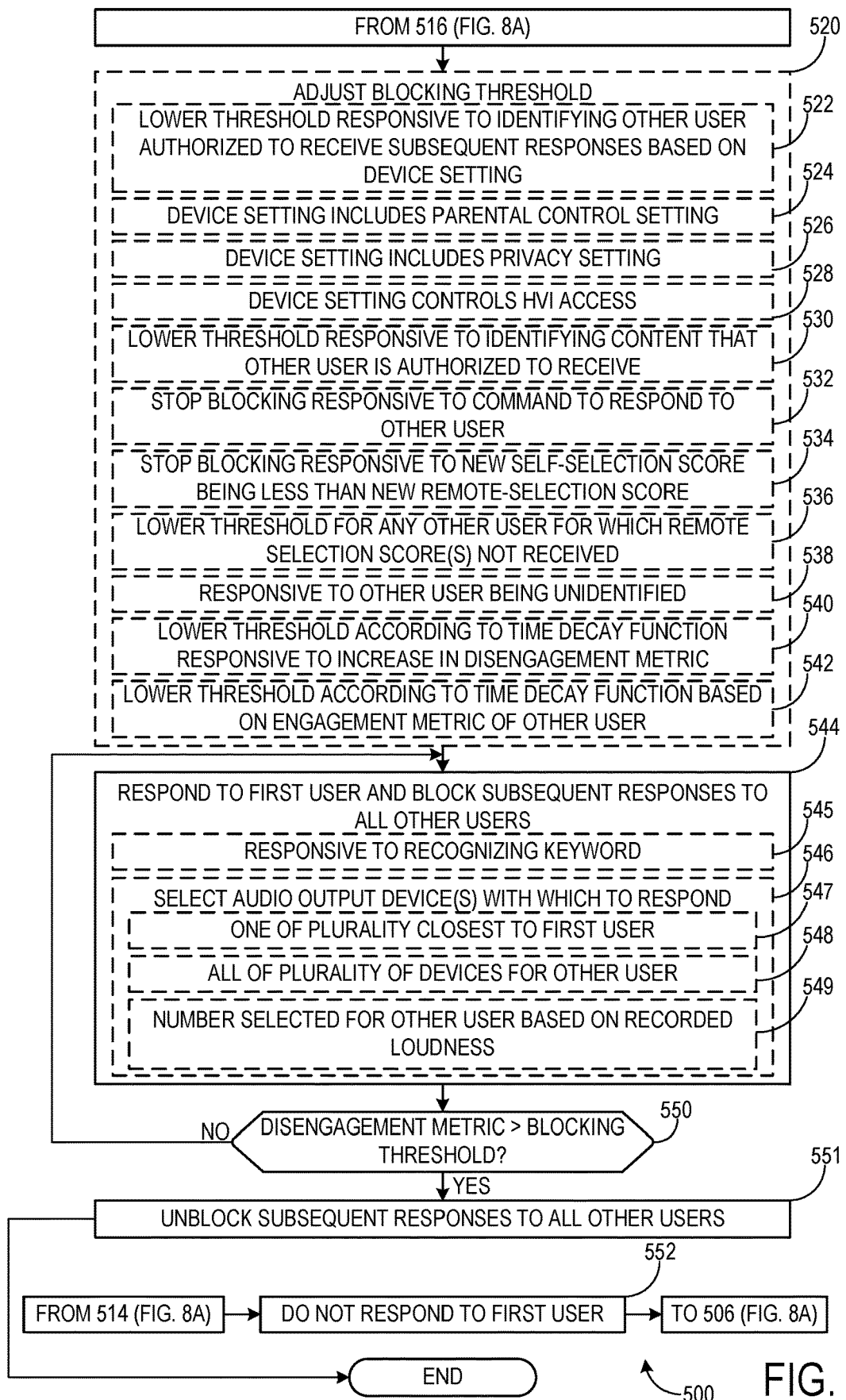

Turning to FIG. 8B, at 520, method 500 optionally includes adjusting a blocking threshold. As described in further detail below, the intelligent assistant may be configured to respond to the first user, and to block subsequent responses to all other users, until the disengagement metric of the first user exceeds the blocking threshold. Thus, the conditions in which subsequent responses to other users are made may be controlled at least in part by adjusting the blocking threshold. Specifically, responses to other users may be made more likely by lowering the blocking threshold (i.e., making it easier for the disengagement metric to exceed the threshold), and less likely by raising the blocking threshold (i.e., making it harder for the disengagement metric to exceed the threshold).

The blocking threshold may be adjusted in any suitable manner, various examples of which are shown in FIG. 8B. For example, as indicated at 522, the blocking threshold may be lowered responsive to identifying another user that is authorized to receive subsequent responses based on a device setting of the intelligent assistant. The device setting may be configured in any suitable manner. Generally, in some examples the device setting may authorize content access through responses for users specifically authorized by the device setting, which may be established by a user or owner of the intelligent assistant. Alternatively or additionally, the device setting may authorize access to specific content identified by a user or owner of the intelligent assistant, where different content may be authorized for different users, in some examples. More specifically, as indicated at 524, the device setting may include a parental control setting authorizing an identified child to receive approved content. For example, the parental control setting may be established by a parent of the child, and may authorize access to specific content deemed appropriate for the child. As indicated at 526, the device setting may include a privacy setting authorizing the other user in the environment to receive selected impersonal content. For example, the intelligent assistant may be implemented on a device that is at least partially personalized to an owner—e.g., a smartphone, laptop, or other device that provides access to content personal to the user, such as email and calendar information. As such, the privacy setting may limit, for users other than the owner, access to impersonal content. As another example, the device may be configured for communal use—e.g., as a game console located in a high-traffic area of an environment.

As indicated at 528, the device setting may authorize the first user to receive high-value information (HVI) based on an organizational relationship between the first user and the HVI, and may authorize the other user to receive filtered content that does not include HVI based on an organizational relationship between the other user and the HVI. For example, the intelligent assistant may be implemented on a device owned by a business and located in a business environment such as a conference room. The device setting may authorize the first user to receive HVI, as the corresponding organizational relationship indicates the first user is an employee of the business authorized to receive HVI. Conversely, the device setting may authorize the other user to receive filtered content not including HVI, as the corresponding organizational relationship indicates the other user is not an employee of the business, where non-employees are not authorized to receive HVI. The intelligent assistant may access organizational relationships stored in a local or remote database, for example. In another example, the device setting may configure the intelligent assistant not to respond to any non-employee.

As indicated at 530, the blocking threshold may be lowered responsive to identifying content that the other user is authorized to receive from the intelligent assistant. The content may be identified responsive to receiving a request from the other user in the environment. In this example, the other user may be identified by the intelligent assistant or may go unidentified. For example, impersonal content for which any user is authorized may prompt lowering of the blocking threshold. As another example, content personalized to the first user of the intelligent assistant may be presented to the other user if the other user is specifically authorized to receive the personal content by the first user.

In response to some select conditions, the intelligent assistant may stop blocking subsequent responses to other users—e.g., the blocking threshold may be set to a minimum (zero) value. For example, as indicated at 532, the intelligent assistant may stop blocking subsequent responses to another user responsive to receiving a command from the first user instructing the intelligent assistant to respond to the other user. The command may include a request for specific information to be provided to the other user, for example. As another example, the command may include a request for the intelligent assistant to listen for a request from the other user. As yet another example, the command may include a request directing the intelligent assistant to learn to recognize (e.g., identify) the other user.

As indicated at 534, the intelligent assistant may stop blocking subsequent responses to another user responsive to a new self-selection score for the first user being less than a new remote-selection score for the first user. In this example, another intelligent assistant may produce the highest selection score among multiple intelligent assistants in an environment, and as such may respond to the first user. To avoid providing responses at two intelligent assistants, and to become available for responding to other users, the intelligent assistant may stop blocking responses to the other user. In operation, the intelligent assistants may determine and exchange selection scores at a frequency that enables changes in their assignment to users to adapt to changing conditions in a non-disruptive manner. For example, by exchanging selection scores at a suitable frequency, the first user may change location—e.g., rooms in an environment—while carrying on a continuous conversation, which is handed off from a first intelligent assistant to a second intelligent assistant in a seamless manner. The frequency may be dynamically adjusted based on a number of factors, including but not limited to, increasing the frequency as more users are detected, increasing frequency with amplitude, signal to noise, and/or other factors indicate a less secure user lock, increasing frequency when identify confidence decreases, and increasing frequency based on a context of the conversation suggesting a user move to a different location or a likelihood that a first user wants to include a second user in a conversation.

As indicated at 536, the intelligent assistant may lower the blocking threshold for any other user for which remote selection scores are not being received. Here, the intelligent assistant recognizes that the other user(s) requests' are not being serviced—e.g., due to existing assignment of other assistants to other users, or an insufficient number of assistants—and accordingly increases the willingness to respond in order to service those requests. To enable this functionality, the intelligent assistants may exchange user identities or a proxy of identity as described above.

As indicated at 538, the intelligent assistant may adjust the blocking threshold responsive to the other user being unidentified. For example, the blocking threshold may be raised, as an unidentified user may be considered a lower priority, or the identification of content for which an unidentified user is authorized may be less likely. As another example, the blocking threshold may be reduced, as the intelligent assistant may be configured to prioritize responses to unidentified users—e.g., when configured to provide information in a public environment.

As indicated at 540, the intelligent assistant may lower the blocking threshold according to a time decay function responsive to an increase in the disengagement metric of the first user. Similar to the adjustment of the disengagement metric according to the time functions described above, the blocking threshold may be reduced (e.g., in an exponentially decaying manner) as an increasing disengagement of the user is indicated (e.g., via image data, eye gaze data, gesture data, audio data). In some examples, the blocking threshold may decrease between instances (e.g., sentences, conversations, time intervals) of recorded speech spoken by the first user according to the time decay function.

As indicated at 542, the intelligent assistant may lower the blocking threshold according to a time decay function based on an engagement metric of the other user. For example, an engagement metric of the other user may indicate increasing engagement or potential engagement of the other user, for which the intelligent assistant prepares by lowering the blocking threshold. The engagement metric may be determined based on one or more of image data, eye gaze data, gesture data, and/or audio data as described above.

At 544, method 500 includes responding to the first user and blocking subsequent responses to all other users until the disengagement metric of the first user exceeds the blocking threshold. As such, requests made by the first user can be coherently and responsively serviced without disruption by speech spoken by other users. However, by identifying circumstances in which it is appropriate to make itself available to respond to other users—in addition to identifying circumstances in which it is appropriate to block responses to other users—the intelligent assistant may retain the ability to service other users' requests without unduly disrupting the first user's interactions with the assistant. In this way, the intelligent assistant may maximize its capability to service multi-user requests in a context-aware manner. As indicated at 545, the intelligent assistant may respond to the first user further responsive to recognizing a keyword in speech spoken by the first user.

In some examples, the intelligent assistant may include or may be operatively coupled to multiple audio output devices. In such examples, the intelligent assistant may select a particular number or set of audio output devices with which to output a response to a user. Thus, responding to the first user and blocking subsequent responses to all other users may optionally include selecting one or more audio output devices controlled by the selected intelligent assistant with which to respond to the first user, as indicated at 546. The audio output device(s) may include speakers 16 of FIG. 1, for example. Selecting one or more audio output devices may include, as indicated at 547, selecting one of a plurality of audio output devices that is recognized as being closest to the first user in the environment.

Figure 9:
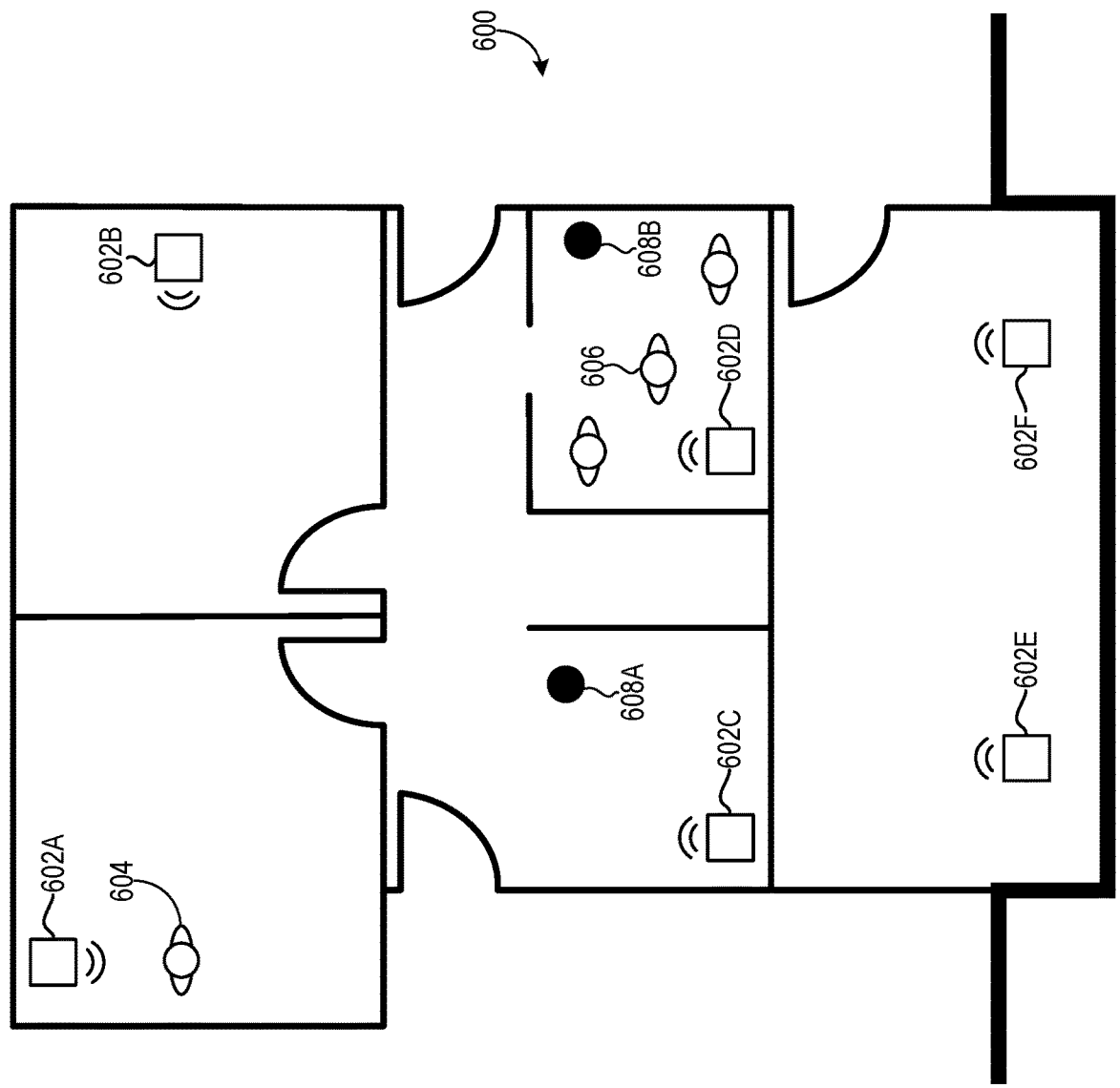
FIG. 9 schematically shows an example environment including a plurality of audio output devices.

To illustrate audio output device selection, FIG. 9 schematically shows a plan view of an example environment 600 comprising a plurality of audio output devices 602. At least one audio output device 602 is placed in each room (e.g., living room, bedroom, kitchen) of environment 600. In this example, an audio output device 602A may be selected for a user 604, as this audio output device is recognized as being closest to the user. Audio output device to user proximity may be determined as described above—e.g., by comparing the amplitudes of audio data streams from a plurality of microphones, by correlating a recognized position of a user with a known or recognized position of an audio output device.

With brief reference to FIG. 8B, selecting one or more audio output devices may include, as indicated at 548, selecting all of a plurality of audio output devices in the environment with which to respond to the other user when the other user is an identified child or an unidentified user. Returning to FIG. 9, it shows another user 606 issuing a request to an intelligent assistant, in response to which all of the audio output devices 602 operatively coupled to the intelligent assistant are used to output a response. The selection of all audio output devices may be desired, and potentially stipulated by a device setting as described above, by a parent of the other user 606 and/or an owner of the intelligent assistant in environment 600 desiring awareness of the other user's interactions with the intelligent assistant—e.g., to ensure those interactions are authorized and/or appropriate.

With brief reference to FIG. 8B, selecting one or more audio output devices may include selecting a number of audio output devices in the environment with which to respond to the other user, where the number is selected based on a recorded loudness in the environment, as indicated at 549. Returning to FIG. 9, the number of audio output devices 602 may be selected based on the loudness in environment 600—e.g., based on a weighted or unweighted average of loudness recorded by microphones in the environment. A greater number of audio output devices 602 may be selected for greater loudness levels in environment 600. In some examples, selection of audio output devices 602 may be at least partially area-specific. For example, audio output device 602C may be selected to respond if the loudness in the associated room is above a threshold. Alternatively or additionally, audio output device 602A may be selected to respond if the loudness in the room associated with audio output device 602C is above a threshold to increase the likelihood that the response is heard, as the loudness in that room may obscure the response from device 602C even if it were selected to respond.

FIG. 9 also illustrates an example in which an intelligent assistant selected to respond to a user based on its selection score may be farther away from another intelligent assistant closer to the user but not selected to respond to the user. For example, an intelligent assistant 608A may be selected to respond to user 606, in lieu of the selection of an intelligent assistant 608B, even if assistant 608B produced a higher selection score. Intelligent assistant 608A may be selected based at least in part on a device setting indicating the assistant as being preferred by the requesting user, for example. As another example, user 606 may have initiated a conversation with intelligent assistant 608A but moved to the location shown in FIG. 9 proximate to intelligent assistant 608B during the conversation. In some examples, the conversation may be transferred to intelligent assistant 608B. However, in other examples the conversation may be retained at intelligent assistant 608A, as conversation from other users proximate assistant 608B is detected. Here, privacy regarding the conversation held by user 606 may be maintained, and/or disruption of the conversation held by the other users proximate intelligent assistant 608B may be avoided. Similarly, output may be transferred from audio output device 602C to audio output device 602D or may be retained at device 602C.

For examples in which multiple audio output devices are capable of outputting responses in an environment such as environment 600, various operational relationships may be established among the audio output devices and multiple intelligent assistants provided in the environment. For example with continued reference to FIG. 9, audio output devices 602 may be controlled by both intelligent assistants 608A and 608B. Under conditions in which an audio output device 602 is in use by one intelligent assistant 608, the other intelligent assistant may select one or more other audio output devices for use in outputting a response. Alternatively or additionally, intelligent assistants 608A and 608B may negotiate to determine which audio output devices 602 are used by which intelligent assistant. Such negotiation may be performed in any suitable manner, and may consider one or more of a user disengagement metric, blocking threshold, response content, request content, selection score, environment loudness, intelligent assistant and/or audio output device to user proximity, and/or other potential considerations.

At 550, method 500 includes determining whether the disengagement metric of the first user exceeds the blocking threshold. If it is determined that the disengagement metric of the first user does exceed the blocking threshold (YES), method 500 proceeds to 551, which includes continuing to respond to the first user without blocking subsequent responses to all other users. If instead it is determined that the disengagement metric of the first user does not exceed the blocking threshold (NO), method 500 returns to 544, which includes continuing to respond to the first user and continuing to block subsequent responses to all other users.

At 552, method 500 includes not responding to the first user if it was determined at 514 that the self-selection score is less than the remote-selection score. Not responding may include not outputting audio including a response, and/or other forms of potential output (e.g., video, light patterns) that another intelligent assistant having the highest selection score may output. Not responding may include keeping a microphone on to continue determining selection scores to thereby retain the ability to respond to a user when a self-selection score is determined for that user that is highest among received selection scores. Thus, method 500 includes returning to 506 following 552 to determine a new self-selection score for the first user. In some examples, not responding may include ceasing transmission of data regarding a recorded audio stream to one or more remote computing devices (e.g., for implementations in which the remote computing device(s) perform at least a portion of method 500). In some examples, not responding may include turning off a microphone and turning the microphone back on after an interval, which may be predetermined, randomized, or determined in response to various conditions (e.g., the microphone may be turned back on in response to a signal received from another intelligent assistant and/or a remote computing device).

It will be appreciated that method 500 is provided as an example, and that any suitable modifications of the method are possible. For example, one or more of the approaches to adjusting the blocking threshold and/or disengagement/engagement metrics may be combined, including combining one or more device settings. Alternative or additional criteria for adjusting the blocking threshold and/or disengagement/engagement metrics may be considered as well. Further, as described in further detail below, one or more portions of method 500—e.g., audio data stream processing, selection scoring, score comparing, blocking threshold adjustment/determination, disengagement/engagement metric adjustment/determination, may be carried out by one or more remote computing devices communicatively coupled to the intelligent assistants described herein.

FIG. 10 shows an example implementation in which one or more remote services 170 perform the natural language processing functionality of intelligent assistant computer 20. In this example, voice listener 30, parser 40, intent handler 50, entity tracker 100 and commitment engine 60 reside on one or more computing devices, such as one or more servers, that are remotely located from a cloud-supported user device A. Sensor data from one or more sensors 22 of the user device A is provided to remote service(s) 170 via a network. For example, audio data of a user speaking may be captured by a microphone of user device A and provided to voice listener 30.

As described above, voice listener 30, parser 40, and intent handler 50 cooperate to convert the audio data into commitments that are stored in commitment engine 60. At a contextually appropriate time, the commitment engine 60 may execute a commitment and provide output, such as audio signals, to one or more output device(s) 70 of the user device A.

FIG. 11 shows another example implementation in which one or more remote services 170 perform the natural language processing functionality of intelligent assistant computer 20. In this example, the one or more remote services 170 are communicatively coupled with a plurality of different sensors 22 and output devices 70. In this example, the sensors include individual standalone sensors A and C, such as microphones, cameras, etc. The output devices include individual standalone output devices B and D, such as loudspeakers.

The one or more remote services 170 are also communicatively coupled to a device E that includes one or more sensors F and an output device G. Device E may take the form of a simple standalone device comprising a microphone, speaker and network connectivity components. In other examples, device E may be a mobile phone, tablet computer, wall-mounted display, or other suitable computing device. In some examples, device E, sensors A and C, and output devices B and D may be part of the same cloud-supported client. In other examples, any number of individual sensors and devices may be utilized with the one or more remote services 170.

As described above, the one or more remote services 170 perform the natural language processing functionality of intelligent assistant computer 20. In some examples, one or more of the remote services 170 may include all of the natural language processing modules of intelligent assistant computer 20, as shown in the example of FIG. 10. In other examples, one or more remote services 170 may include less than all of the natural language processing modules, and may be communicatively coupled to the other modules located at one or more other service(s). In the present example, one or more of the remote services 170 also may comprise a device selector 174 that may utilize sensor inputs to select output device B, D and/or G to receive output from the commitment engine 60.

Device selector 174 may be configured to implement at least a portion of selection module 80 (FIG. 7) and method 500 (FIGS. 8A-8B). For example, device selector 174 may receive audio data streams from multiple intelligent assistants located in an environment, determine selection scores for each assistant, identify the assistant that produced the highest score, and cause transmission of an instruction to the highest-scoring assistant to respond to a requesting user in the environment. In other examples, the intelligent assistants may determine respective selection scores and transmit the scores to the remote services 170, which may identify the highest-scoring assistant and transmit an instruction to that assistant causing its response to the requesting user. Further, device selector 174 may determine/adjust one or more user disengagement/engagement metrics and/or a blocking threshold. Still further, device selector 174 may select one or more audio output devices with which to respond to a requesting user as described above.

In some embodiments, the methods and processes described herein may be tied to a computing system of one or more computing devices. In particular, such methods and processes may be implemented as a computer-application program or service, an application-programming interface (API), a library, and/or other computer-program product.

Figure 12:
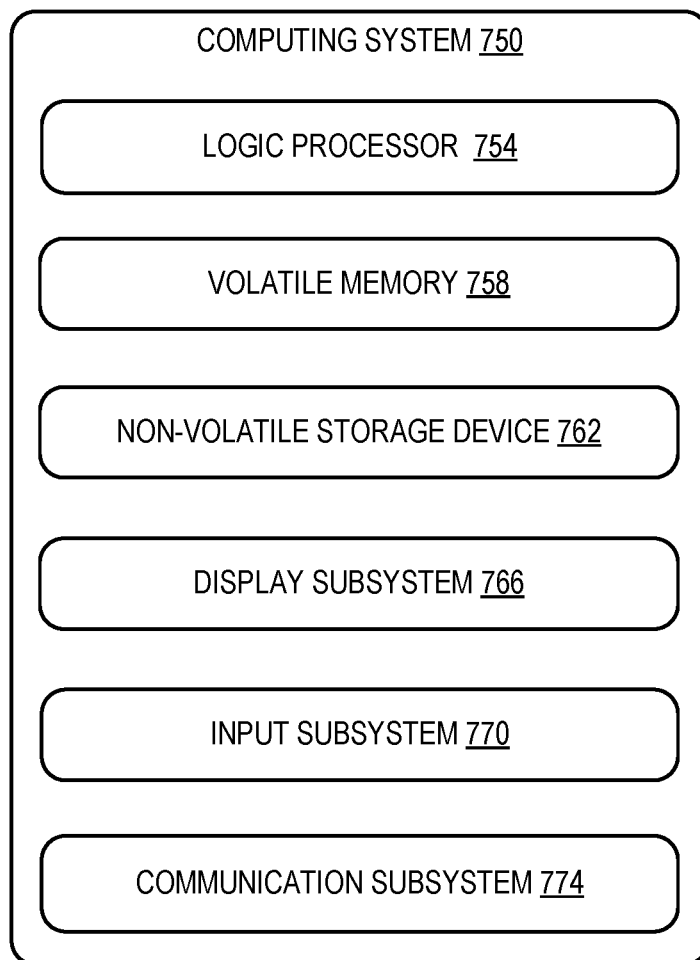
FIG. 12 schematically shows a computing system according to examples of the present disclosure.

FIG. 12 schematically shows a non-limiting embodiment of a computing system 750 that can enact one or more of the methods and processes described above. Computing system 750 is shown in simplified form. Computing system 750 may take the form of one or more intelligent assistant computers, personal computers, server computers, tablet computers, home-entertainment computers, network computing devices, gaming devices, mobile computing devices, mobile communication devices (e.g., smartphone), and/or other computing devices. As non-limiting examples, any or all of the computing devices described above (e.g., all-in-one computing device 10, sensors 22, voice listener 30, parser 40, intent handler 50, commitment engine 60, output device 70, entity tracker 100, all-in-one computing device 160, remote computing devices 162, and/or remote services 170) may be implemented as computing system 750.

Computing system 750 includes a logic processor 754, volatile memory 758, and a non-volatile storage device 762. Computing system 600 may optionally include a display subsystem 766, input subsystem 770, communication subsystem 774, and/or other components not shown in FIG. 12.

Logic processor 754 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor 754 may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 754 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor 754 may be virtualized and executed by remotely accessible, networked computing devices configured in a cloud-computing configuration. In such a case, these virtualized aspects may be run on different physical logic processors of various different machines.

Volatile memory 758 may include physical devices that include random access memory. Volatile memory 758 is typically utilized by logic processor 754 to temporarily store information during processing of software instructions. It will be appreciated that volatile memory 758 typically does not continue to store instructions when power is cut to the volatile memory.

Non-volatile storage device 762 includes one or more physical devices configured to hold instructions executable by the logic processors to implement the methods and processes described herein. When such methods and processes are implemented, the state of non-volatile storage device 762 may be transformed—e.g., to hold different data.

Non-volatile storage device 762 may include physical devices that are removable and/or built-in. Non-volatile storage device 762 may include optical memory (CD, DVD, HD-DVD, Blu-Ray Disc, etc.), semiconductor memory (ROM, EPROM, EEPROM, FLASH memory, etc.), and/or magnetic memory (hard-disk drive, floppy-disk drive, tape drive, MRAM, etc.), or other mass storage device technology. Non-volatile storage device 762 may include nonvolatile, dynamic, static, read/write, read-only, sequential-access, location-addressable, file-addressable, and/or content-addressable devices. It will be appreciated that non-volatile storage device 762 is configured to hold instructions even when power is cut to the non-volatile storage device.

Aspects of logic processor 754, volatile memory 758, and non-volatile storage device 762 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module", "program" and "engine" may be used to describe an aspect of computing system 750 implemented to perform a particular function. In some cases, a module, program or engine may be instantiated via logic processor 754 executing instructions held by non-volatile storage device 762, using portions of volatile memory 758. It will be understood that different modules, programs or engines may be instantiated from the same application, service, code block, object, library, routine, API, function, etc. Likewise, the same module, program or engine may be instantiated by different applications, services, code blocks, objects, routines, APIs, functions, etc. The terms modules, programs and engines encompass individual or groups of executable files, data files, libraries, drivers, scripts, database records, etc.

It will be appreciated that a "service", as used herein, is an application program that may be executable across multiple user sessions. A service may be available to one or more system components, programs, and/or other services. In some implementations, a service may run on one or more server-computing devices.

When included, display subsystem 766 may be used to present a visual representation of data held by non-volatile storage device 762. As the herein described methods and processes change the data held by the non-volatile storage device, and thus transform the state of the non-volatile storage device, the state of display subsystem 766 may likewise be transformed to visually represent changes in the underlying data. Display subsystem 766 may include one or more display devices utilizing virtually any type of technology. Such display devices may be combined with logic processor 754, volatile memory 758, and/or non-volatile storage device 762 in a shared enclosure, or such display devices may be peripheral display devices.

When included, input subsystem 770 may comprise or interface with one or more user-input devices. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection, gaze detection, and/or intent recognition; electric-field sensing componentry for assessing brain activity; any of the sensors described with respect to the example use cases and environments discussed above; and/or any other suitable sensor.

When included, communication subsystem 774 may be configured to communicatively couple computing system 750 with one or more other computing devices. Communication subsystem 774 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 750 to send and receive data to and from other devices via a network such as the Internet.

Another example provides an intelligent assistant computer comprising a logic machine, and a storage machine holding instructions executable by the logic machine to recognize another intelligent assistant computer located in a same environment as the intelligent assistant computer, record speech spoken by a first user, determine a self-selection score for the first user based on the speech spoken by the first user, send the self-selection score for the first user to the other intelligent assistant computer, receive a remote-selection score for the first user from the other intelligent assistant computer, compare the self-selection score for the first user to the remote-selection score for the first user, if the self-selection score is greater than the remote-selection score, respond to the first user and block subsequent responses to all other users until a disengagement metric of the first user exceeds a blocking threshold, and if the self-selection score is less than the remote-selection score, do not respond to the first user. In such an example, the instructions alternatively or additionally may be executable to set the disengagement metric of the first user to a maximum value responsive to an explicit command from the first user to disengage from the intelligent assistant computer. In such an example, the instructions alternatively or additionally may be executable to lower the blocking threshold responsive to identifying another user that is authorized to receive subsequent responses based on a device setting of the intelligent assistant computer. In such an example, the device setting alternatively or additionally may include a parental control setting authorizing an identified child to receive approved content. In such an example, the device setting alternatively or additionally may include a privacy setting authorizing the other user to receive selected impersonal content. In such an example, the device setting alternatively or additionally may authorize the first user to receive high-value information based on an organizational relationship between the first user and the high-value information, and may authorize the other user to receive filtered content that does not include high-value information based on a different organizational relationship between the other user and the high-value information. In such an example, the instructions alternatively or additionally may be further executable to receive a request from another user in the environment, identify content that the other user is authorized to receive from the intelligent assistant computer, and responsive to identifying the content, lower the blocking threshold. In such an example, the instructions alternatively or additionally may be executable to stop blocking subsequent responses to another user responsive to receiving a command from the first user instructing the intelligent assistant computer to respond to the other user. In such an example, the instructions alternatively or additionally may be executable to stop blocking subsequent responses to another user responsive to a new self-selection score for the first user being less than a new remote-selection score for the first user. In such an example, the instructions alternatively or additionally may be executable to lower the blocking threshold for any other user for which remote selection scores are not being received. In such an example, the instructions alternatively or additionally may be executable to respond to the first user responsive to recognizing a keyword in the speech spoken by the first user. In such an example, the instructions alternatively or additionally may be executable to adjust the blocking threshold responsive to the other user being unidentified. In such an example, the other intelligent assistant computer alternatively or additionally may be closer to the first user than the intelligent assistant computer. In such an example, the instructions alternatively or additionally may be executable to lower the blocking threshold according to a time decay function. In such an example, the instructions alternatively or additionally may be executable to lower the blocking threshold according to a time decay function based on one or both of the disengagement metric of the first user and an engagement metric of the other user. In such an example, the instructions alternatively or additionally may be executable to select one of a plurality of audio output devices controlled by the intelligent assistant computer with which to respond to the first user. In such an example, the instructions alternatively or additionally may be executable to select all of a plurality of audio output devices controlled by the intelligent assistant computer with which to respond to the other user when the other user is an identified child or an unidentified user. In such an example, the instructions alternatively or additionally may be executable to select a number of audio output devices controlled by the intelligent assistant computer with which to respond to the other user, the number being selected based on a recorded loudness in the environment.

Another example provides, at an intelligent assistant computer, a method, comprising recognizing another intelligent assistant computer located in a same environment as the intelligent assistant, recording speech spoken by a first user, determining a self-selection score for the first user based on the speech spoken by the first user, sending the self-selection score for the first user to the other intelligent assistant computer, receiving a remote-selection score for the first user from the other intelligent assistant computer, comparing the self-selection score for the first user to the remote-selection score for the first user, if the self-selection score is greater than the remote-selection score, responding to the first user and blocking subsequent responses to all other users until a disengagement metric of the first user exceeds a blocking threshold, and if the self-selection score is less than the remote-selection score, not responding to the first user.

Another example provides, at an intelligent assistant computer, a method, comprising recognizing another intelligent assistant computer located in a same environment as the intelligent assistant, recording speech spoken by a first user, determining a self-selection score for the first user based on the speech spoken by the first user, sending the self-selection score for the first user to the other intelligent assistant computer, receiving a remote-selection score for the first user from the other intelligent assistant computer, comparing the self-selection score for the first user to the remote-selection score for the first user, if the self-selection score is greater than the remote-selection score, responding to the first user and blocking subsequent responses to all other users until a disengagement metric of the first user exceeds a blocking threshold, wherein the blocking threshold decreases between instances of recorded speech spoken by the first user according to a time decay function, and if the self-selection score is less than the remote-selection score, not responding to the first user.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. An intelligent assistant computer, comprising:
   a logic machine; and
   a storage machine holding instructions executable by the logic machine to:
      recognize another intelligent assistant computer located in a same environment as the intelligent assistant computer;
      record speech spoken by a first user;
      determine a self-selection score for the first user based on the speech spoken by the first user;
      send the self-selection score for the first user to the other intelligent assistant computer;
      receive a remote-selection score for the first user from the other intelligent assistant computer;
      compare the self-selection score for the first user to the remote-selection score for the first user;
      if the self-selection score is greater than the remote-selection score, respond to the first user, determine a disengagement metric of the first user based on recorded speech spoken by the first user, and block subsequent responses to all other users until the disengagement metric of the first user exceeds a blocking threshold, wherein the disengagement metric increases with increasing disengagement of the first user from the intelligent assistant computer, wherein subsequent responses to all other users are blocked when the blocking threshold is above the disengagement metric, and wherein a subsequent response to another user is not blocked when the blocking threshold is below the disengagement metric;
      if the self-selection score is less than the remote-selection score, do not respond to the first user; and
      stop blocking subsequent responses to the other user responsive to a new self-selection score for the first user being less than a new remote-selection score for the first user.

2. The intelligent assistant computer of claim 1, wherein the instructions are further executable to set the disengagement metric of the first user to a maximum value responsive to an explicit command from the first user to disengage from the intelligent assistant computer.

3. The intelligent assistant computer of claim 1, wherein the instructions are further executable to lower the blocking threshold responsive to identifying that the other user is authorized to receive subsequent responses based on a device setting of the intelligent assistant computer.

4. The intelligent assistant computer of claim 3, wherein the device setting includes a parental control setting authorizing an identified child to receive approved content.

5. The intelligent assistant computer of claim 3, wherein the device setting includes a privacy setting authorizing the other user to receive selected impersonal content.

6. The intelligent assistant computer of claim 3, wherein the device setting authorizes the first user to receive high-value information based on an organizational relationship between the first user and the high-value information, and authorizes the other user to receive filtered content that does not include high-value information based on a different organizational relationship between the other user and the high-value information.

7. The intelligent assistant computer of claim 1, wherein the instructions are further executable to:
   receive a request from the other user;
   identify content that the other user is authorized to receive from the intelligent assistant computer; and
   responsive to identifying the content, lower the blocking threshold.

8. The intelligent assistant computer of claim 1, wherein the instructions are further executable to stop blocking subsequent responses to the other user responsive to receiving a command from the first user instructing the intelligent assistant computer to respond to the other user.

9. The intelligent assistant computer of claim 1, wherein the instructions are further executable to lower the blocking threshold for any other user for which remote selection scores are not being received.

10. The intelligent assistant computer of claim 1, wherein the instructions are further executable to respond to the first user responsive to recognizing a keyword in the speech spoken by the first user.

11. The intelligent assistant computer of claim 1, wherein the instructions are further executable to adjust the blocking threshold responsive to the other user being unidentified.

12. The intelligent assistant computer of claim 1, wherein the other intelligent assistant computer is closer to the first user than the intelligent assistant computer.

13. The intelligent assistant computer of claim 1, wherein the instructions are further executable to lower the blocking threshold according to a time decay function.

14. The intelligent assistant computer of claim 13, wherein the instructions are further executable to lower the blocking threshold according to the time decay function based on one or both of the disengagement metric of the first user and an engagement metric of the other user.

15. The intelligent assistant computer of claim 1, wherein the instructions are further executable to select one of a plurality of audio output devices controlled by the intelligent assistant computer with which to respond to the first user.

16. The intelligent assistant computer of claim 15, wherein the instructions are further executable to select all of the plurality of audio output devices controlled by the intelligent assistant computer with which to respond to the other user when the other user is an identified child or an unidentified user.

17. The intelligent assistant computer of claim 1, wherein the instructions are further executable to select a number of audio output devices controlled by the intelligent assistant computer with which to respond to the other user, the number being selected based on a recorded loudness in the environment.

18. At an intelligent assistant computer, a method, comprising:
   recognizing another intelligent assistant computer located in a same environment as the intelligent assistant;
   recording speech spoken by a first user;
   determining a self-selection score for the first user based on the speech spoken by the first user;
   sending the self-selection score for the first user to the other intelligent assistant computer;
   receiving a remote-selection score for the first user from the other intelligent assistant computer;
   comparing the self-selection score for the first user to the remote-selection score for the first user;
   if the self-selection score is greater than the remote-selection score, responding to the first user, determining a disengagement metric of the first user based on recorded speech spoken by the first user, and blocking subsequent responses to all other users until the disengagement metric of the first user exceeds a blocking threshold, wherein the disengagement metric increases with increasing disengagement of the first user from the intelligent assistant computer, and wherein subsequent responses to all other users are blocked when the blocking threshold is above the disengagement metric, wherein a subsequent response to another user is not blocked when the blocking threshold is below the disengagement metric;
   if the self-selection score is less than the remote-selection score, not responding to the first user; and
   stopping blocking subsequent responses to the other user responsive to a new self-selection score for the first user being less than a new remote-selection score for the first user.

19. At an intelligent assistant computer, a method, comprising:
   recognizing another intelligent assistant computer located in a same environment as the intelligent assistant;
   recording speech spoken by a first user;
   determining a self-selection score for the first user based on the speech spoken by the first user;
   sending the self-selection score for the first user to the other intelligent assistant computer;
   receiving a remote-selection score for the first user from the other intelligent assistant computer;
   comparing the self-selection score for the first user to the remote-selection score for the first user;
   if the self-selection score is greater than the remote-selection score, responding to the first user, determining a disengagement metric of the first user based on recorded speech spoken by the first user, and blocking subsequent responses to all other users until the disengagement metric of the first user exceeds a blocking threshold, wherein the disengagement metric increases with increasing disengagement of the first user from the intelligent assistant computer, wherein subsequent responses to all other users are blocked when the blocking threshold is above the disengagement metric, wherein a subsequent response to another user is not blocked when the blocking threshold is below the disengagement metric, and wherein the blocking threshold decreases between instances of recorded speech spoken by the first user according to a time decay function;
   if the self-selection score is less than the remote-selection score, not responding to the first user; and
   stopping blocking subsequent responses to the other user responsive to a new self-selection score for the first user being less than a new remote-selection score for the first user.

* * * * *